(12) United States Patent
Bruszewski et al.

(10) Patent No.: US 8,052,741 B2
(45) Date of Patent: Nov. 8, 2011

(54) BRANCH VESSEL PROSTHESIS WITH A ROLL-UP SEALING ASSEMBLY

(75) Inventors: Walter Bruszewski, Guerneville, CA (US); Masoumeh Mafi, Mountain View, CA (US); Shahram Shamlou, Mountain View, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 12/409,012

(22) Filed: Mar. 23, 2009

(65) Prior Publication Data
US 2010/0241218 A1 Sep. 23, 2010

(51) Int. Cl.
*A61F 2/06* (2006.01)
(52) U.S. Cl. ...................... 623/1.35; 606/153
(58) Field of Classification Search ............. 623/1.13, 623/1.16, 1.11, 1.15, 1.18, 1.53, 1.22, 1.3, 623/1.31, 1.14, 1.35–1.36, 1.42, 1.24, 1.26; 606/153, 151, 144, 149
See application file for complete search history.

(56) References Cited

U.S. PATENT DOCUMENTS

| | | | |
|---|---|---|---|
| 4,733,665 A | 3/1988 | Palmaz | |
| 4,800,882 A | 1/1989 | Gianturco | |
| 4,886,062 A | 12/1989 | Wiktor | |
| 5,133,732 A | 7/1992 | Wiktor | |
| 5,292,331 A | 3/1994 | Boneau | |
| 5,366,462 A * | 11/1994 | Kaster et al. ................. | 606/153 |
| 5,421,955 A | 6/1995 | Lau et al. | |
| 5,713,917 A | 2/1998 | Leonhardt et al. | |
| 5,824,041 A | 10/1998 | Lenker et al. | |
| 5,827,242 A | 10/1998 | Follmer et al. | |
| 5,868,777 A * | 2/1999 | Lam ............................. | 606/194 |
| 5,935,162 A | 8/1999 | Dang | |
| 6,036,702 A * | 3/2000 | Bachinski et al. ........... | 606/153 |
| 6,090,127 A | 7/2000 | Globerman | |
| 6,120,534 A * | 9/2000 | Ruiz ............................ | 623/1.19 |
| 6,187,033 B1 * | 2/2001 | Schmitt et al. .............. | 623/1.35 |
| 6,287,339 B1 * | 9/2001 | Vazquez et al. ............. | 623/2.4 |
| 6,334,864 B1 * | 1/2002 | Amplatz et al. ............ | 606/200 |

(Continued)

FOREIGN PATENT DOCUMENTS
GB 2437058 10/2007
(Continued)

OTHER PUBLICATIONS

U.S. Appl. No. 11/939,106, filed Nov. 13, 2007, Bruszewski et al.

*Primary Examiner* — Alvin J. Stewart

(57) ABSTRACT

A branch prosthesis configured for placement in a branch vessel includes an expandable tubular body portion, an expandable annular flange attached to a proximal end of the body portion, and a sealing sleeve proximally extending from the annular flange. The sealing sleeve is adapted to deform to a generally straight cylindrical hollow shape during implantation. When deployed, the sealing sleeve rolls up to a tightly-wound coil that bears against the annular flange. When used in conjunction with a main prosthesis having a side opening and deployed within in a main vessel, the annular flange of the branch prosthesis engages an outer surface of the main prosthesis around a perimeter of the side opening and the sealing sleeve engages an inner surface of the main prosthesis around the perimeter of the side opening to form a fluid-tight seal between the main prosthesis and the branch prosthesis.

22 Claims, 15 Drawing Sheets

U.S. PATENT DOCUMENTS

| | | | |
|---|---|---|---|
| 6,451,048 B1* | 9/2002 | Berg et al. | 623/1.13 |
| 6,488,701 B1 | 12/2002 | Nolting et al. | |
| 6,517,558 B2* | 2/2003 | Gittings et al. | 606/153 |
| 6,607,551 B1 | 8/2003 | Sullivan et al. | |
| 6,652,567 B1 | 11/2003 | Deaton | |
| 6,660,015 B1* | 12/2003 | Berg et al. | 606/153 |
| 6,695,878 B2* | 2/2004 | McGuckin et al. | 623/1.19 |
| 6,719,781 B1* | 4/2004 | Kim | 623/1.13 |
| 6,730,116 B1 | 5/2004 | Wolinsky et al. | |
| 6,827,736 B2* | 12/2004 | Perouse | 623/1.36 |
| 6,926,690 B2* | 8/2005 | Renati | 604/8 |
| 6,962,602 B2* | 11/2005 | Vardi et al. | 623/1.11 |
| 6,994,713 B2* | 2/2006 | Berg et al. | 606/153 |
| 7,048,751 B2 | 5/2006 | Vargas et al. | |
| 7,201,772 B2* | 4/2007 | Schwammenthal et al. | 623/2.18 |
| 7,211,095 B2* | 5/2007 | Bachinski et al. | 606/153 |
| 7,264,632 B2 | 9/2007 | Wright et al. | |
| 7,320,702 B2* | 1/2008 | Hammersmark et al. | 623/1.11 |
| 7,326,242 B2* | 2/2008 | Eidenschink | 623/1.15 |
| 7,341,598 B2* | 3/2008 | Davidson et al. | 623/1.35 |
| 7,429,269 B2* | 9/2008 | Schwammenthal et al. | 623/2.14 |
| 7,452,372 B2* | 11/2008 | Miller | 623/1.35 |
| 7,455,677 B2* | 11/2008 | Vargas et al. | 606/153 |
| 7,655,037 B2* | 2/2010 | Fleming et al. | 623/1.36 |
| 7,670,369 B2* | 3/2010 | Schaeffer | 623/1.31 |
| 7,731,741 B2* | 6/2010 | Eidenschink | 623/1.11 |
| 7,731,747 B2* | 6/2010 | Kaplan et al. | 623/1.35 |
| 7,744,643 B2* | 6/2010 | Hegg | 623/1.35 |
| 7,749,245 B2* | 7/2010 | Cohn et al. | 606/200 |
| 7,753,949 B2* | 7/2010 | Lamphere et al. | 623/1.26 |
| 7,758,633 B2* | 7/2010 | Nazzaro | 623/1.3 |
| 7,766,955 B2* | 8/2010 | Vardi et al. | 623/1.15 |
| 7,780,686 B2* | 8/2010 | Park et al. | 606/153 |
| 7,837,727 B2* | 11/2010 | Goetz et al. | 623/2.18 |
| 2001/0003161 A1* | 6/2001 | Vardi et al. | 623/1.11 |
| 2002/0052643 A1* | 5/2002 | Wholey et al. | 623/1.13 |
| 2002/0151913 A1* | 10/2002 | Berg et al. | 606/153 |
| 2002/0156517 A1* | 10/2002 | Perouse | 623/1.11 |
| 2002/0193871 A1* | 12/2002 | Beyersdorf et al. | 623/1.26 |
| 2002/0198585 A1* | 12/2002 | Wisselink | 623/1.11 |
| 2003/0093145 A1* | 5/2003 | Lawrence-Brown et al. | 623/1.21 |
| 2004/0030348 A1* | 2/2004 | Peterson et al. | 606/153 |
| 2004/0059406 A1 | 3/2004 | Cully et al. | |
| 2004/0088007 A1* | 5/2004 | Eidenschink | 607/1 |
| 2004/0102797 A1* | 5/2004 | Golden et al. | 606/153 |
| 2004/0133268 A1* | 7/2004 | Davidson et al. | 623/1.35 |
| 2004/0138737 A1* | 7/2004 | Davidson et al. | 623/1.35 |
| 2004/0158267 A1* | 8/2004 | Sancoff et al. | 606/153 |
| 2004/0193192 A1 | 9/2004 | Bachinski et al. | |
| 2004/0204749 A1 | 10/2004 | Gunderson | |
| 2004/0225306 A1* | 11/2004 | Blatter et al. | 606/153 |
| 2004/0267290 A1* | 12/2004 | Baker et al. | 606/153 |
| 2005/0021060 A1* | 1/2005 | Davis et al. | 606/153 |
| 2005/0080437 A1* | 4/2005 | Wright | 606/153 |
| 2005/0154444 A1 | 7/2005 | Quadri | |
| 2005/0182430 A1* | 8/2005 | Schenck | 606/153 |
| 2006/0025790 A1* | 2/2006 | de Winter et al. | 606/153 |
| 2006/0069401 A1* | 3/2006 | Wright | 606/153 |
| 2006/0100684 A1* | 5/2006 | Elliott | 623/1.2 |
| 2006/0122691 A1* | 6/2006 | Richter | 623/1.16 |
| 2006/0122692 A1* | 6/2006 | Gilad et al. | 623/1.24 |
| 2006/0155359 A1* | 7/2006 | Watson | 623/1.13 |
| 2006/0184227 A1 | 8/2006 | Rust | |
| 2006/0224169 A1* | 10/2006 | Weisenburgh et al. | 606/153 |
| 2006/0229643 A1* | 10/2006 | Nolan et al. | 606/153 |
| 2006/0282106 A1* | 12/2006 | Cole et al. | 606/153 |
| 2007/0021757 A1* | 1/2007 | Ortiz | 606/153 |
| 2007/0061003 A1* | 3/2007 | Shmulewitz et al. | 623/1.16 |
| 2007/0067011 A1* | 3/2007 | Krolik et al. | 623/1.11 |
| 2007/0088425 A1* | 4/2007 | Schaeffer | 623/1.13 |
| 2007/0106313 A1* | 5/2007 | Golden et al. | 606/153 |
| 2007/0142902 A1* | 6/2007 | Yadin | 623/1.16 |
| 2007/0191872 A1* | 8/2007 | Stiger | 606/153 |
| 2007/0208415 A1* | 9/2007 | Grotheim et al. | 623/1.16 |
| 2007/0213813 A1* | 9/2007 | Von Segesser et al. | 623/2.18 |
| 2008/0243151 A1* | 10/2008 | Binmoeller et al. | 606/153 |
| 2008/0262518 A1* | 10/2008 | Freudenthal | 606/151 |
| 2008/0262595 A1 | 10/2008 | Chu et al. | |
| 2008/0269784 A1* | 10/2008 | Abbott et al. | 606/144 |
| 2009/0240320 A1* | 9/2009 | Tuval et al. | 623/1.24 |
| 2009/0326641 A1* | 12/2009 | Davis et al. | 623/1.15 |
| 2010/0063521 A1* | 3/2010 | Manzo | 606/153 |

FOREIGN PATENT DOCUMENTS

| | | |
|---|---|---|
| WO | WO99/18887 | 4/1999 |
| WO | WO2007/028112 | 3/2007 |
| WO | WO2008/112415 | 9/2008 |
| WO | WO2009/129079 | 10/2009 |
| WO | WO2009/131823 | 10/2009 |

\* cited by examiner

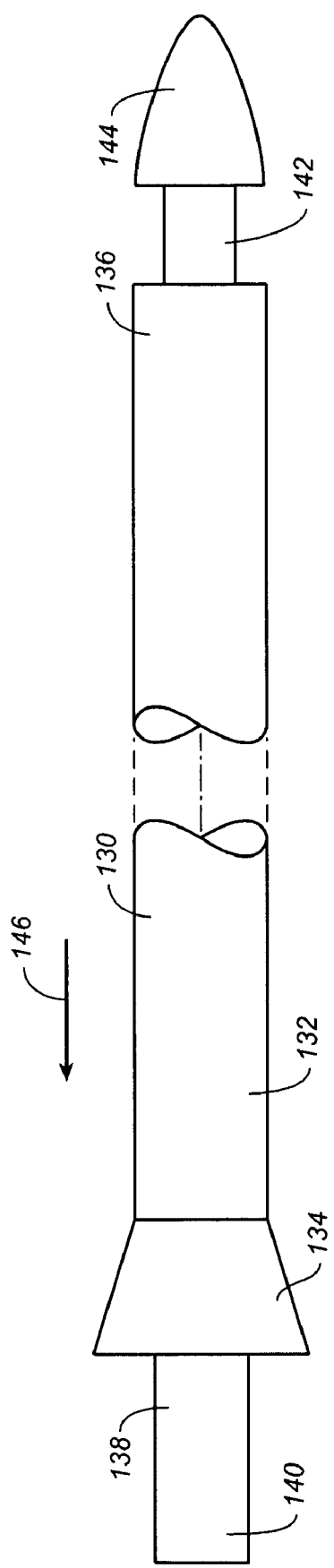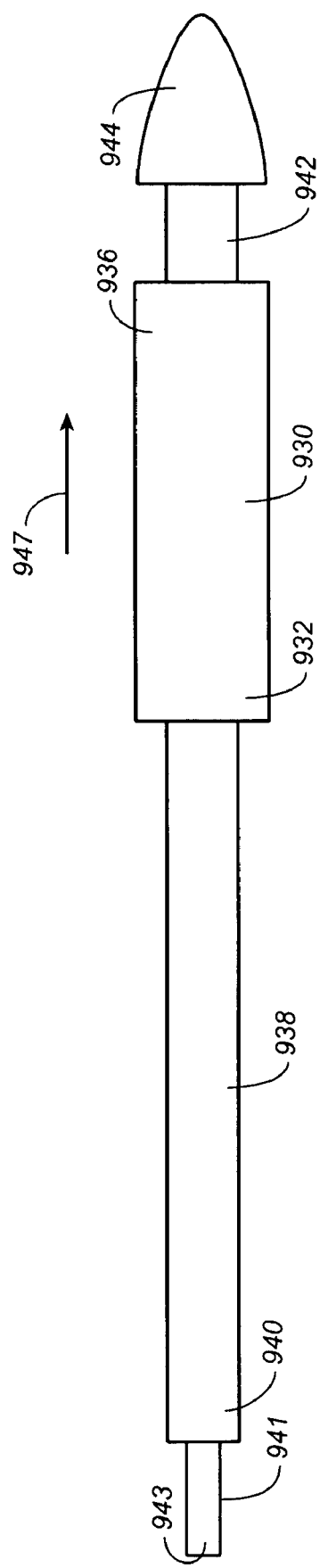

BRANCH VESSEL PROSTHESIS WITH A ROLL-UP SEALING ASSEMBLY

FIELD OF THE INVENTION

This invention relates generally to endoluminal medical devices and procedures, and more particularly to a branch vessel prosthesis having a rollup flange for creating a fluid-tight seal with a main vessel prosthesis.

BACKGROUND

Prostheses for implantation in blood vessels or other similar organs of the living body are, in general, well known in the medical art. For example, prosthetic vascular grafts constructed of biocompatible materials, such as Dacron or expanded, porous polytetrafluoroethylene (PTFE) tubing, have been employed to replace or bypass damaged or occluded natural blood vessels. In general, endovascular grafts typically include a graft anchoring component that operates to hold the tubular graft in its intended position within the blood vessel. Most commonly, the graft anchoring component is one or more radially compressible stents that are radially expanded in situ to anchor the tubular graft to the wall of a blood vessel or anatomical conduit. Thus, endovascular grafts are typically held in place by mechanical engagement and friction due to the opposition forces provided by the expandable stents.

In general, rather than performing an open surgical procedure to implant a graft that may be traumatic and invasive, stent grafts are preferably deployed through a less invasive intraluminal delivery. More particularly, a lumen of the vasculature is accessed at a convenient and low trauma entry point, and the compressed stent graft is routed through the vasculature to the site where the prosthesis is to be deployed. Intraluminal deployment of the self expanding device is typically effected using a delivery catheter with coaxial inner and outer tubes arranged for relative axial movement. For example, a self-expanding stent graft may be compressed and disposed within the distal end of an outer catheter tube distal of a stop fixed to the inner member. The catheter is then routed though a body lumen until the end of the catheter containing the stent graft is positioned at the intended treatment site. The stop on the inner member is then held stationary while the outer tube of the delivery catheter is withdrawn. The stop prevents the stent graft from being withdrawn with the sheath. As the sheath is withdrawn, the stent graft is released from the confines of the sheath and radially self-expands so that at least a portion of it contacts and substantially conforms to a portion of the surrounding interior wall of the lumen, e.g., the blood vessel wall or anatomical conduit.

Grafting procedures are also known for treating aneurysms. Aneurysms result from weak, thinned blood vessel walls that "balloon" or expand due to aging, disease and/or blood pressure in the vessel. Consequently, aneurysmal vessels have a potential to rupture, causing internal bleeding and potentially life threatening conditions. Grafts are often used to isolate aneurysms or other blood vessel abnormalities from normal blood pressure, reducing pressure on the weakened vessel wall and reducing the chance of vessel rupture. As such, a tubular endovascular graft may be placed within the aneurysmal blood vessel to create an artificial flow conduit through the aneurysm, thereby reducing if not nearly eliminating the exertion of blood pressure on the aneurysm.

While aneurysms can occur in any blood vessel, most occur in the aorta and peripheral arteries. Depending on the region of the aorta involved, the aneurysm may extend into areas having vessel bifurcations or segments of the aorta from which smaller "branch" arteries extend. Various types of aortic aneurysms may be classified on the basis of the region of aneurysmal involvement. For example, thoracic aortic aneurysms include aneurysms present in the ascending thoracic aorta, the aortic arch, and branch arteries that emanate therefrom, such as subclavian arteries, and also include aneurysms present in the descending thoracic aorta and branch arteries that emanate therefrom, such as thoracic intercostal arteries and/or the suprarenal abdominal aorta and branch arteries that emanate therefrom, such as renal, superior mesenteric, celiac and/or intercostal arteries. Lastly, abdominal aortic aneurysms include aneurysms present in the aorta below the diaphragm, e.g., pararenal aorta and the branch arteries that emanate therefrom, such as the renal arteries.

Unfortunately, not all patients diagnosed with aortic aneurysms are presently considered to be candidates for endovascular grafting. This is largely due to the fact that most of the endovascular grafting systems of the prior art are not designed for use in regions of the aorta from which side branches extend. The deployment of endovascular grafts within regions of the aorta from which branch arteries extend presents additional technical challenges because, in those cases, the endovascular graft must be designed, implanted, and maintained in a manner which does not impair the flow of blood into the branch arteries.

To accommodate side branches, a main vessel stent graft having a fenestration or opening in a side wall thereof is often utilized. The fenestration is positioned to align with the ostium of the branch vessel after deployment. In use, the proximal end of the graft having one or more side openings is securely anchored in place, and the fenestrations or openings are configured and deployed to avoid blocking or restricting blood flow into the side branches. Fenestrations alone do not form discrete conduit(s) through which blood is channeled into each side branch artery. As a result, the edges of the graft surrounding the fenestrations are prone to: i) the leakage of blood into the space between the outer surface of the aortic graft and the surrounding aortic wall; or ii) post-implantation migration or movement of the stent graft causing misalignment of the fenestration(s) and the branch artery(ies), which may result in impaired flow into the branch artery(ies).

In some cases, another stent graft, often referred to as a branch graft, may then be deployed through the fenestration into the branch vessel to provide a conduit for blood flow to the branch vessel. The branch graft is preferably sealingly connected to the main graft in situ to prevent undesired leakage.

An especially challenging area to deploy and seal branch grafts is the aortic arch. In a significant population of patients with thoracic aortic aneurysms (TAA), there is no healthy vessel tissue for fixation and sealing of stent grafts distal to the branches of the aortic arch. Thus, a stent graft deployed in the aortic arch spans across one or more branch arteries.

Thus, there remains a need in the art for improvements for directing flow from fenestrations to the corresponding branch vessels. Embodiments hereof relate to a side branch prosthesis having a mobile and resilient sealing assembly to provide a blood tight seal between the side branch vessel prosthesis and a prosthesis implanted within a main vessel. The sealing assembly may be utilized in conjunction with pre-fenestrated grafts or grafts having fenestrations created in situ.

SUMMARY OF THE INVENTION

A side branch intraluminal prosthesis includes an expandable tubular body portion with a first outer diameter, the body portion having a proximal end and a distal end. The branch prosthesis also includes an expandable annular flange attached to the proximal end of the body portion, the flange having a second outer diameter that is greater than the first diameter, and a sealing sleeve extending proximally from the expandable flange. The sealing sleeve is adapted to be deformed in a first configuration during implantation and to deploy to a second configuration after implantation. The sealing sleeve is a generally straight cylindrical hollow shape having a low profile sufficient for delivery to a target site in the first configuration. The sealing sleeve rolls up into a tightly-wound coil that bears against the annular flange in the second configuration.

The side branch prosthesis is configured for placement in a branch vessel and configured for use in conjunction with a main vessel prosthesis having a side opening and deployed within in a main vessel. When deployed, the annular flange engages an outer surface of the main vessel prosthesis around a perimeter of the side opening and the rolled up sealing sleeve engages an inner surface of the main prosthesis around the perimeter of the side opening to form a fluid-tight seal between the main vessel prosthesis and the branch vessel prosthesis.

BRIEF DESCRIPTION OF DRAWINGS

The foregoing and other features and advantages of embodiments according to the invention will be apparent from the following description as illustrated in the accompanying drawings. The accompanying drawings, which are incorporated herein and form a part of the specification, further serve to explain the principles of the embodiments and to enable a person skilled in the pertinent art to make and use the described embodiments herein. The drawings are not to scale.

FIG. 8 is an example of a branch prosthesis delivery device according to an embodiment hereof.

FIG. 9 is an example of a branch prosthesis delivery device according to another embodiment hereof.

DETAILED DESCRIPTION

Specific embodiments are now described with reference to the figures, wherein like reference numbers indicate identical or functionally similar elements. Unless otherwise indicated, with respect to intravascular prostheses described herein such as branch prosthesis 100, the terms "distal" and "proximal" are used in the following description with respect to a position or direction relative to the heart. "Distal" and "distally" are positions distant from or in a direction away from the heart by blood flow path, and "proximal" and "proximally" are positions near or in a direction toward the heart by blood flow path. With respect to delivery systems described herein, the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician.

The following detailed description is merely exemplary in nature. Although the description is in the context of treatment of a blood vessel (e.g., aorta) from which branch blood vessels (e.g., carotid, innominate, subclavian, intercostal, superior mesenteric, celiac, renal or iliac arteries) extend, the embodiments may also be used in any other body passageways where they are deemed useful. Furthermore, there is no intention to be bound by any expressed or implied theory presented in the preceding technical field, background, brief summary or the following detailed description.

Figure 1:
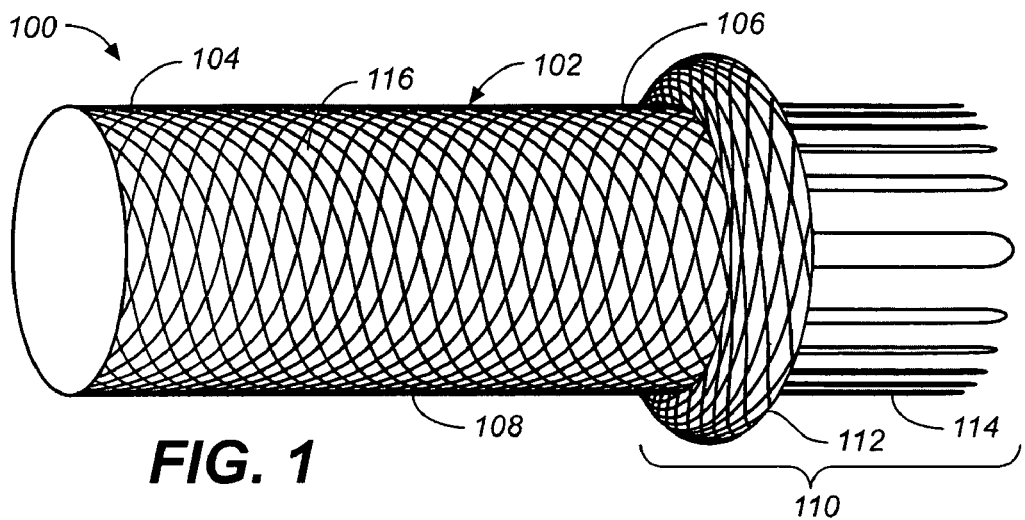
FIG. 1 is a schematic illustration of a branch prosthesis according to an embodiment hereof, wherein a sealing sleeve of the branch prosthesis is in an undeployed configuration.
Figure 2:
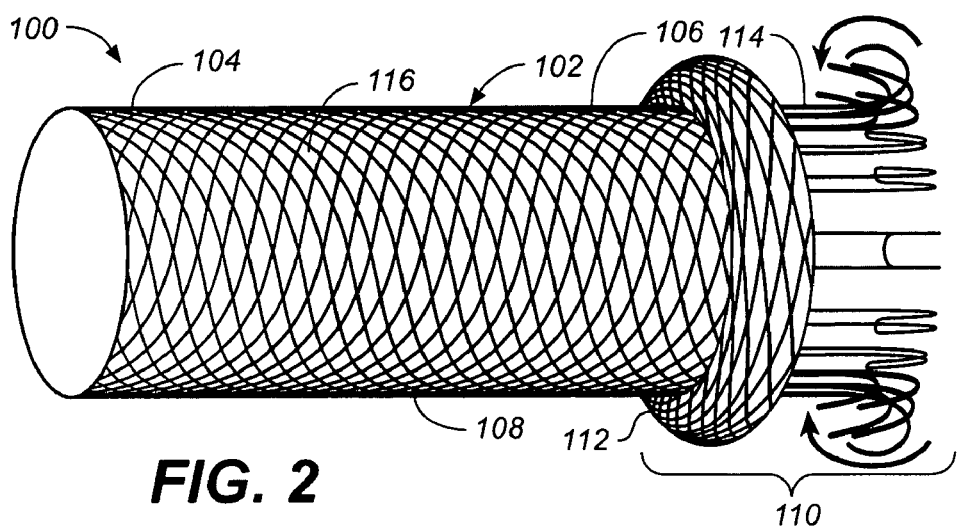
FIG. 2 is a schematic illustration of the branch prosthesis of FIG. 1, showing the sealing sleeve having begun to deploy.
Figure 3:
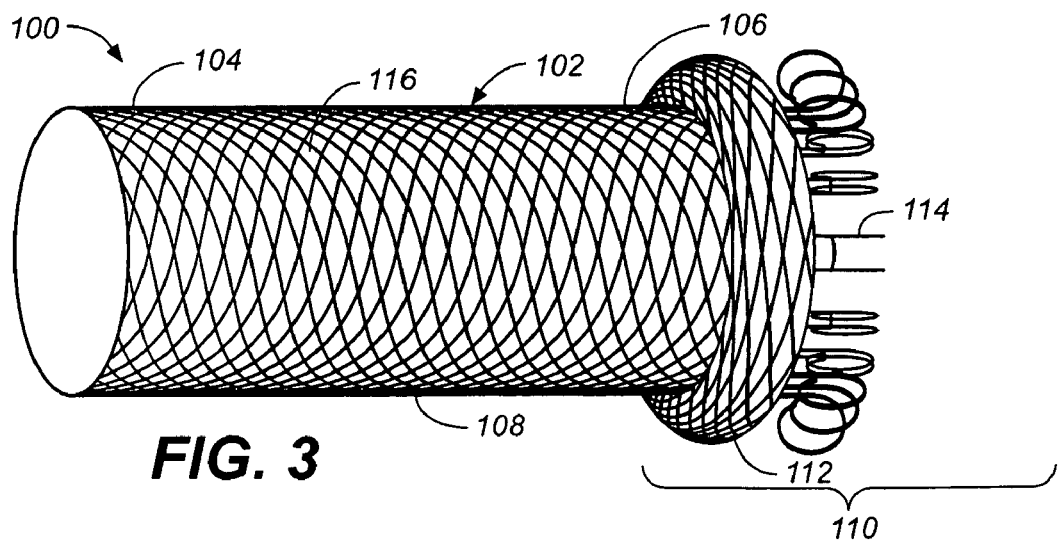
FIG. 3 is a schematic illustration of the branch prosthesis of FIG. 1, wherein the sealing sleeve is fully deployed in its rolled-up or coiled configuration.

With reference to FIGS. 1-3, a prosthesis 100 configured for placement in a branch vessel includes a body portion 102 having an outer diameter 108 extends between a distal end portion 104 and a proximal end portion 106. Branch prosthesis 100 includes a sealing assembly 110 attached to proximal end portion 106. Sealing assembly 110 includes an expandable annular flange 112 and a sealing sleeve 114 proximally extending from annular flange 112. Sealing sleeve 114 is adapted to be deformed in a first configuration during implantation and to deploy to a second configuration during implantation. The first configuration of sealing sleeve 114 (shown in FIG. 1) is a generally straight cylindrical hollow shape. FIG. 1 shows sealing sleeve 114 in an undeployed configuration, while FIG. 2 illustrates sealing sleeve 114 when it has begun to deploy to the second configuration. When fully deployed, as shown in FIG. 3, sealing sleeve 114 rolls up to a tightly-wound annular coil that bears against annular flange 112. When used in conjunction with a main prosthesis deployed within in a main vessel and having a side opening or fenestration, sealing assembly 110 forms a fluid-tight seal between branch prosthesis 100 and the main prosthesis, as will be explained in further detail herein.

Figure 4A:
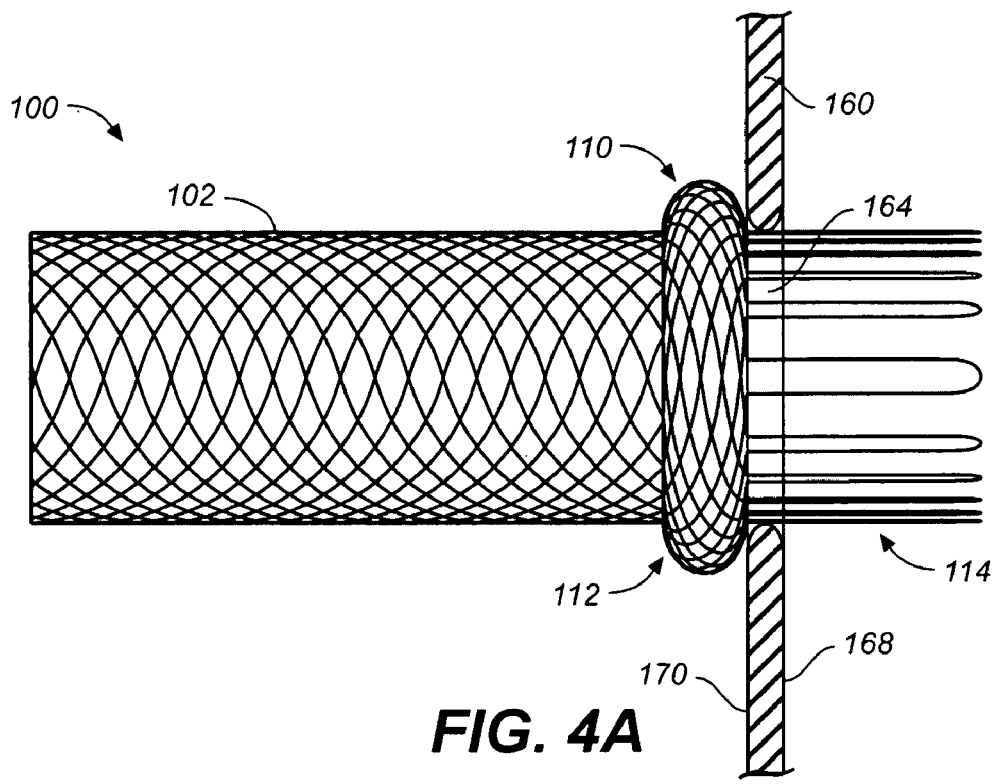
FIG. 4A is a side cross-sectional view schematic illustration of the branch prosthesis of FIG. 1 in a fluid-tight sealing arrangement with a main vessel prosthesis, wherein a sealing sleeve of the branch prosthesis is in an undeployed configuration.
Figure 4B:
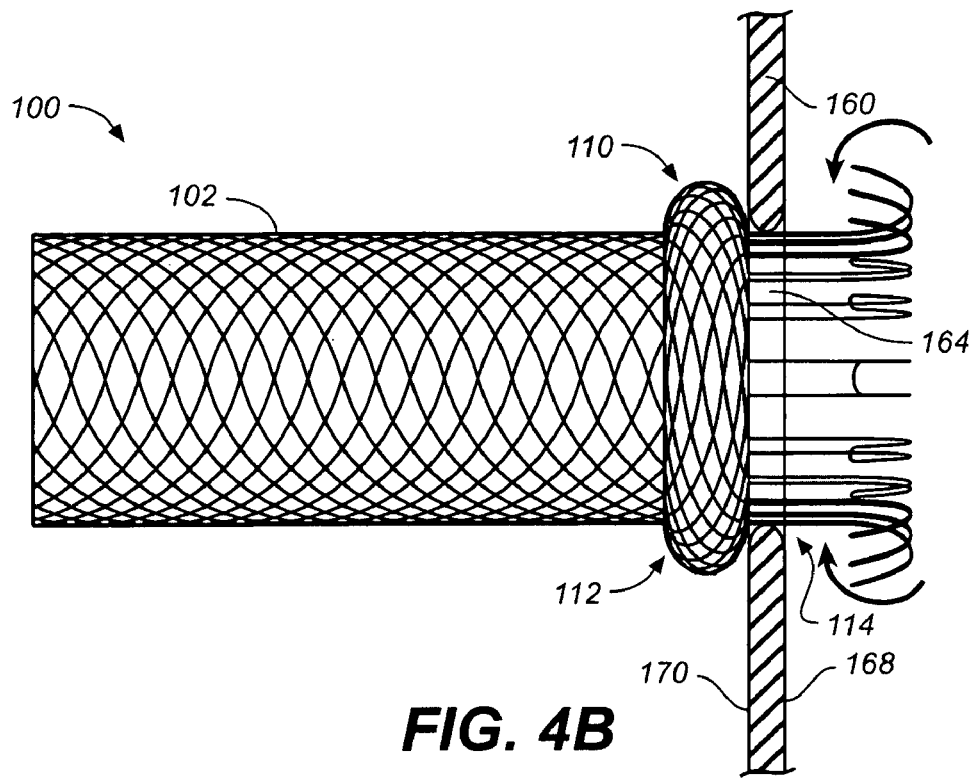
FIG. 4B is a side cross-sectional view schematic illustration of the branch prosthesis of FIG. 1 in a fluid-tight sealing arrangement with a main vessel prosthesis, showing the sealing sleeve having begun to deploy.
Figure 4C:
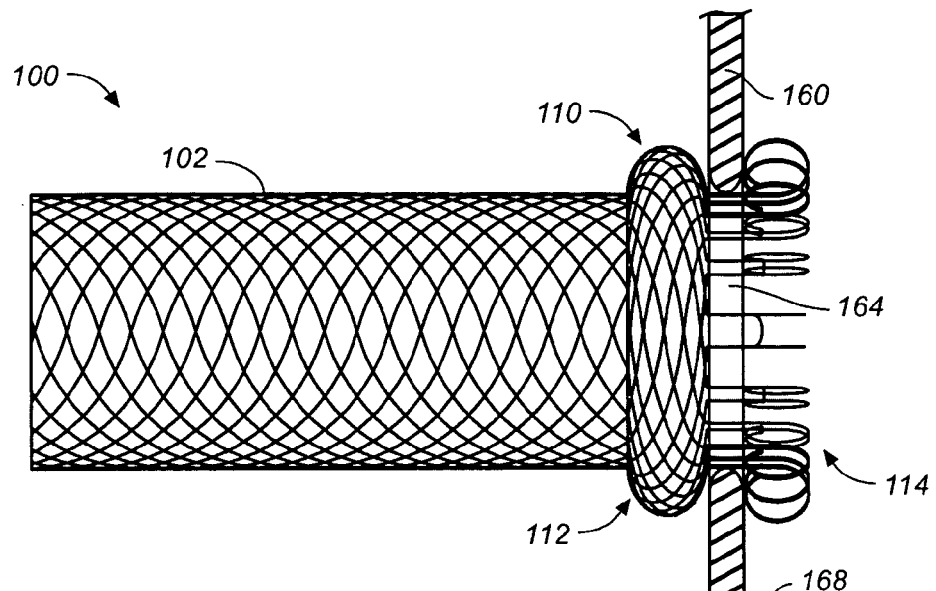
FIG. 4C is a side cross-sectional view schematic illustration of the branch prosthesis of FIG. 1 in a fluid-tight sealing arrangement with a main vessel prosthesis, wherein the sealing sleeve is fully deployed in its rolled-up or coiled configuration.

More particularly, referring now to FIGS. 4A-4C, annular flange 112 is deployed to engage an outer surface 170 of a main prosthesis 160 around a perimeter of a fenestration 164 and sealing sleeve 114 is deployed to engage an inner surface 168 of main prosthesis 160 around the perimeter of fenestration 164, thus forming a constantly-loaded, gasket-type seal between main prosthesis 160 and branch prosthesis 100. Sealing sleeve 114 captures the material of main prosthesis 160 and presses it against annular flange 112, thus forming a resilient sealing assembly 110.

Deployment of branch prosthesis 100 is facilitated by constructing both tubular body 102 and sealing assembly 110 out of a self-expanding spring-type or superelastic material that has a shape memory. Shape memory may be imparted to branch prosthesis 100 by thermal treatment to achieve a spring temper in stainless steel, for example, or to set a shape memory in a susceptible metal alloy, such as nickel-titanium (nitinol). Branch prosthesis 100 may be introduced into a body lumen inside a sleeve or sheath that surrounds and mechanically holds branch prosthesis 100 in a compressed, reduced size which facilitates advancement of branch prosthesis 100 through the vasculature to the treatment site within a body vessel. When the prosthesis is positioned within the body lumen at the treatment site such as, for example, within the target side branch vessel, a delivery sleeve containing the device is moved to release branch prosthesis 100, releasing the branch prosthesis 100 to radially expand and engage the wall of the vessel lumen. Non-exhaustive examples of suitable self-expanding materials for branch prosthesis include nickel-titanium (nitinol), stainless steel, cobalt based alloys (605L, MP35N), titanium, tantalum, and self-expanding polymeric materials.

Body portion 102 is a generally tubular or cylindrical braided structure that is configured to fit into a body lumen such as a blood vessel. It will be appreciated by one of ordinary skill in the art that the braided configuration of tubular body portion 102 shown in FIGS. 1-3 is merely exemplary and that other configurations may be utilized with sealing assembly 110. Body portion 102 is expandable between a compressed state or configuration that enables branch prosthesis 100 to be intraluminally delivered to the target site, and then be expanded or deployed to a second configuration where the prosthesis contacts a vessel wall. The cross-sectional shape of body portion 102 is generally circular. However, the cross-sectional shape may alternatively be ellipsoidal, rectangular, hexagonal rectangular, square, or other polygon tubular shape. When expanded, outer diameter 108 of body portion 102 may be approximately equal to or slightly larger than an inner diameter of a target body vessel and may be substantially constant along the length body portion 102. Branch prosthesis 100 may be utilized in any suitable anatomical conduit, including but not limited to branches of the thoracic aorta or branches of the abdominal aorta. When intended for placement in branches of the thoracic aorta, outer diameter 108 will generally range between 8 mm-14 mm. When intended for placement in branches of the abdominal aorta, outer diameter 108 will generally range between 5 mm-8 mm. In one embodiment, body portion 102 of branch prosthesis 100 may have a length between 40 mm-60 mm.

Figure 15:
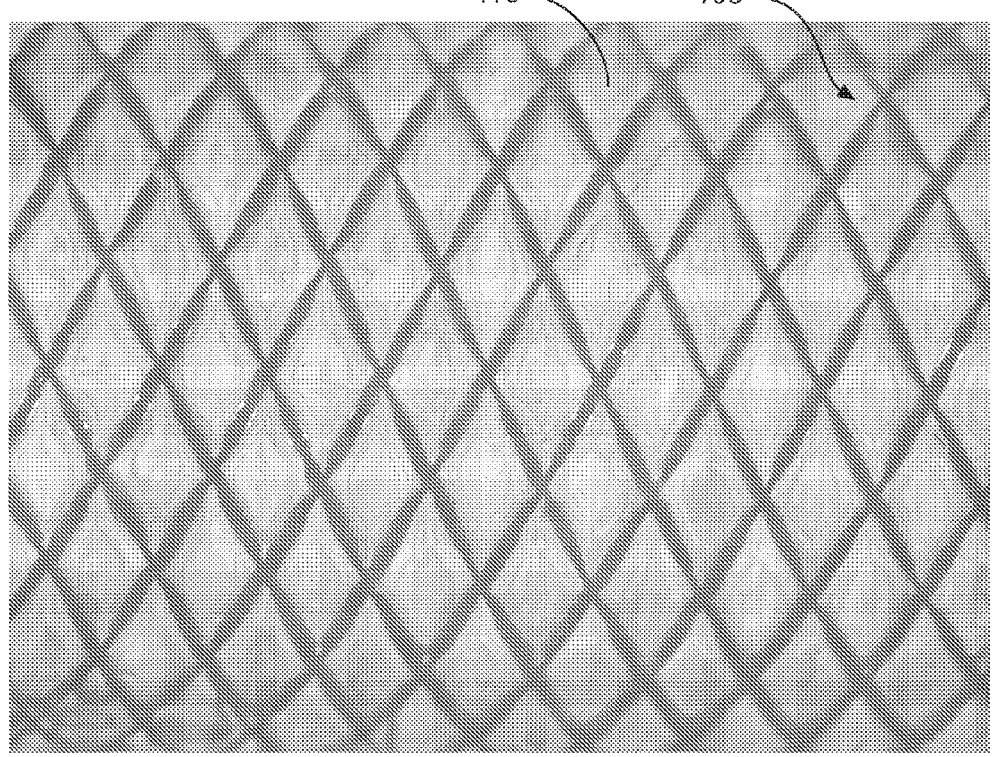
FIG. 15 is an enlarged view of the skeletal frame of FIG. 14, wherein the skeletal frame further includes a polymeric graft material.

In one embodiment, tubular body portion 102 includes a graft material 116 attached thereto such that at least body portion 102 is substantially impermeable to fluids and creates a one-way fluid passage. Graft material 116 is thin-walled so that branch prosthesis 100 may be compressed into a small diameter, yet is capable of acting as a strong, leak-resistant fluid conduit when branch prosthesis 100 is expanded to a cylindrical tubular form. In one embodiment (see embodiment of FIG. 15), graft material 116 is a coating of PTFE (polytetrafluoroethylene), ePTFE, polyurethane polymers, siloxane polymers, polycarbonate urethanes, silicone, or another suitable polymer. For example, as will be understood by one of ordinary skill in the art, tubular body 102 may be made impermeable by elastomer impregnation, lamination of elastomer film, or lamination of ePTFE/PTFE film. An exemplary coating for tubular body 102 is disclosed in U.S. Pat. No. 6,488,701 to Nolting, herein incorporated by reference in its entirety. Graft material 116 may alternatively be a low-porosity woven fabric, such as polyester or Dacron fabric, attached to tubular body 102.

Similar to tubular body portion 102, annular flange 112 is expandable between a compressed state (first diameter) that enables branch prosthesis 100 to be intraluminally delivered to the target site, and an expanded or deployed state (second diameter) configured to be positioned at an ostium of a branch vessel and to contact an outer surface of a prosthesis implanted in a main vessel. Annular flange 112 expands to a second diameter, which is greater than diameter 108 of tubular body portion 102. Thus, annular flange 112 may be considered a flared end attached to or continuous with tubular body portion 102.

Figure 7A:
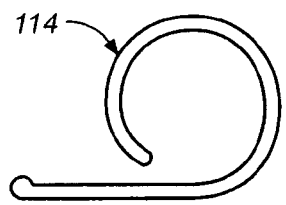
FIG. 7A is a schematic cross-sectional view of an edge of the sealing sleeve of the branch prosthesis deployed in its rolled-up or coiled configuration, taken along line A-A of FIG. 7.
Figure 5:
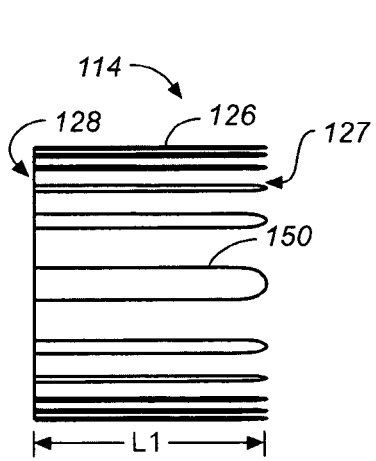
FIG. 5 is a side schematic illustration of the sealing sleeve of the branch prosthesis in a straight, undeployed configuration.
Figure 6:
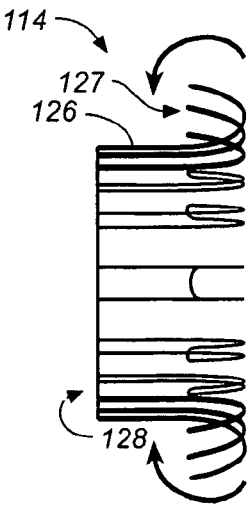
FIG. 6 is a side schematic illustration of the sealing sleeve of the branch prosthesis once it has begun to deploy.
Figure 7:
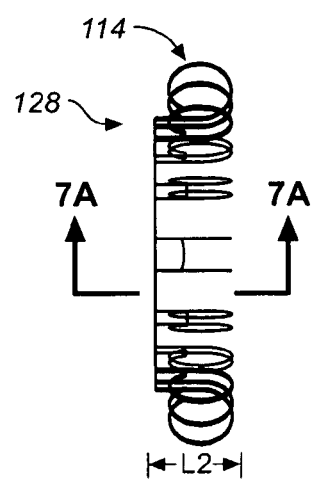
FIG. 7 is a side schematic illustration of the sealing sleeve of the branch prosthesis fully deployed in its rolled-up or coiled configuration.

Referring now to FIGS. 5-7, sealing sleeve 114 will be described in more detail. As previously described, sealing sleeve 114 is adapted to be deformed into a first configuration when constrained within a delivery system during implantation. FIG. 5 is a side view schematic of sealing sleeve 114 of branch prosthesis 100 in the first configuration of a generally straight cylinder 126. Cylinder 126 has a first end 127 and a second end 128. In one embodiment, sealing sleeve 114 in the first deformed configuration of generally straight cylinder 126 has a length L1 between 1 cm-3 cm. Although not shown in FIG. 5, second end 128 is continuous with annular flange 112 such that cylinder 126 extends proximally from annular flange 112. Sealing sleeve 114 includes generally straight filaments 150 having loops or turns at first end 127. While the generally straight filaments 150 are shown relatively widely separated in the figure, they could be alternatively be configured to be closely side by side to be indistinguishable from a single wire or alternately a single wire may be connected to the main body of the branch prosthesis by welding, crimping, or as a single wire extension of the filaments of the main body, to act as the sealing sleeve using single wire strands.

FIG. 6 is a side view schematic of sealing sleeve 114 as it begins to deploy into the second configuration. When released from the constraint of the delivery device, first end 127 of cylinder 126 begins to roll up or curl upon itself towards second end 128, similar to a rolled up stocking or sock. As apparent from FIG. 6, as sealing sleeve 114 rolls up into a coil, the length of cylinder 126 decreases. FIGS. 7 and 7A illustrate sealing sleeve 114 in its second configuration, after being fully deployed and allowed to recover its shape-set rolled-up or coiled configuration. FIG. 7A is a cross-sectional view of sealing sleeve 114, taken along line A-A of FIG. 7. When deployed, sealing sleeve 114 rolls up to a tightly-wound coil that bears against annular flange 112. As apparent from FIG. 7, the rolled-up sealing sleeve 114 is substantially shorter than generally straight cylinder 126. In addition, the rolled-up sealing sleeve 114 has a larger outer diameter than an outer diameter in the first deformed configuration of generally straight cylinder 126.

Figure 14:
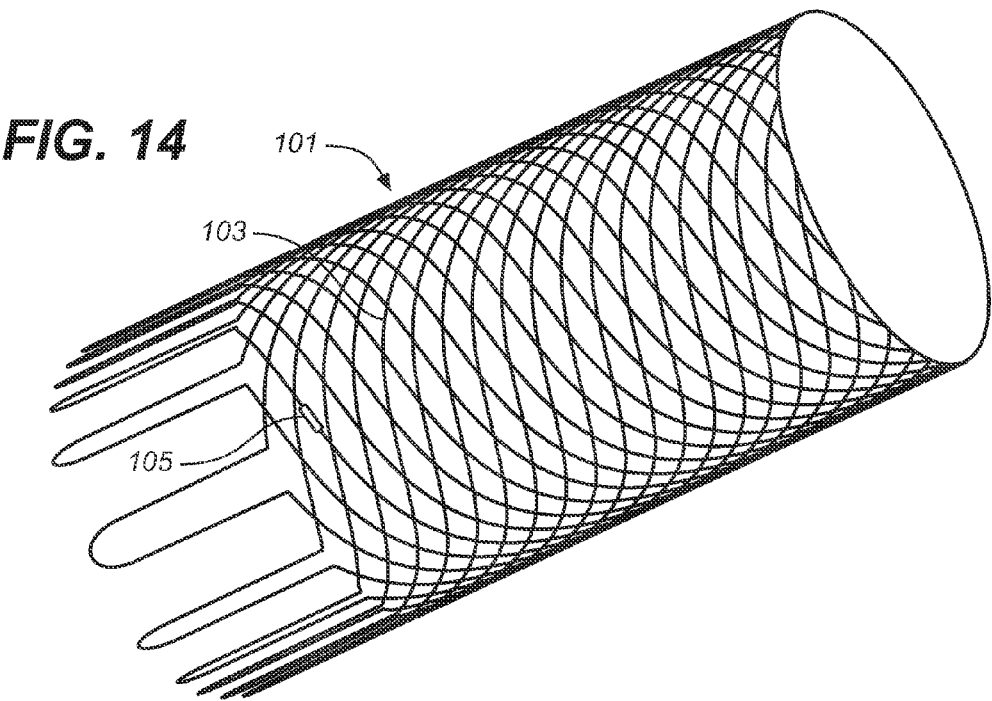
FIG. 14 is a schematic illustration of a skeletal frame formed from a single wire, wherein the skeletal frame may be the basis of a branch prosthesis according to an embodiment hereof.

In one embodiment hereof, branch prosthesis 100 may be a unitary structure integrally formed from a single wire nitinol (NiTi) braid. For example, as shown in FIG. 14, a skeletal frame 101 is hollow, cylindrical structure formed from a single wire 103. A braided or mesh portion forming tubular body 102 is located on approximately one half of skeletal frame 101, and filaments 150 (described above with respect to FIG. 5) are positioned on the other half of skeletal frame 101. Wire 103 is temporarily attached to and wound around a cylindrical mandrel (not shown) in order to provide the desirable braided configuration of FIG. 14. The ends of the single wire 103 are welded or crimped together at a joint 105. Single wire 103 is generally circular in cross-section although it may be square, rectangular, D-shaped or any other shape. As described above, at least a portion of skeletal frame 101 may be coated with a polymeric graft material 116 as shown in the enlarged view of FIG. 15 so that at least a portion of the branch prosthesis is substantially impermeable to fluids. In one embodiment, the entire length of skeletal frame 101 may be covered with graft material or made impermeable by elastomer impregnation, lamination of elastomer film, or lamination of ePTFE/PTFE film.

Figure 16:
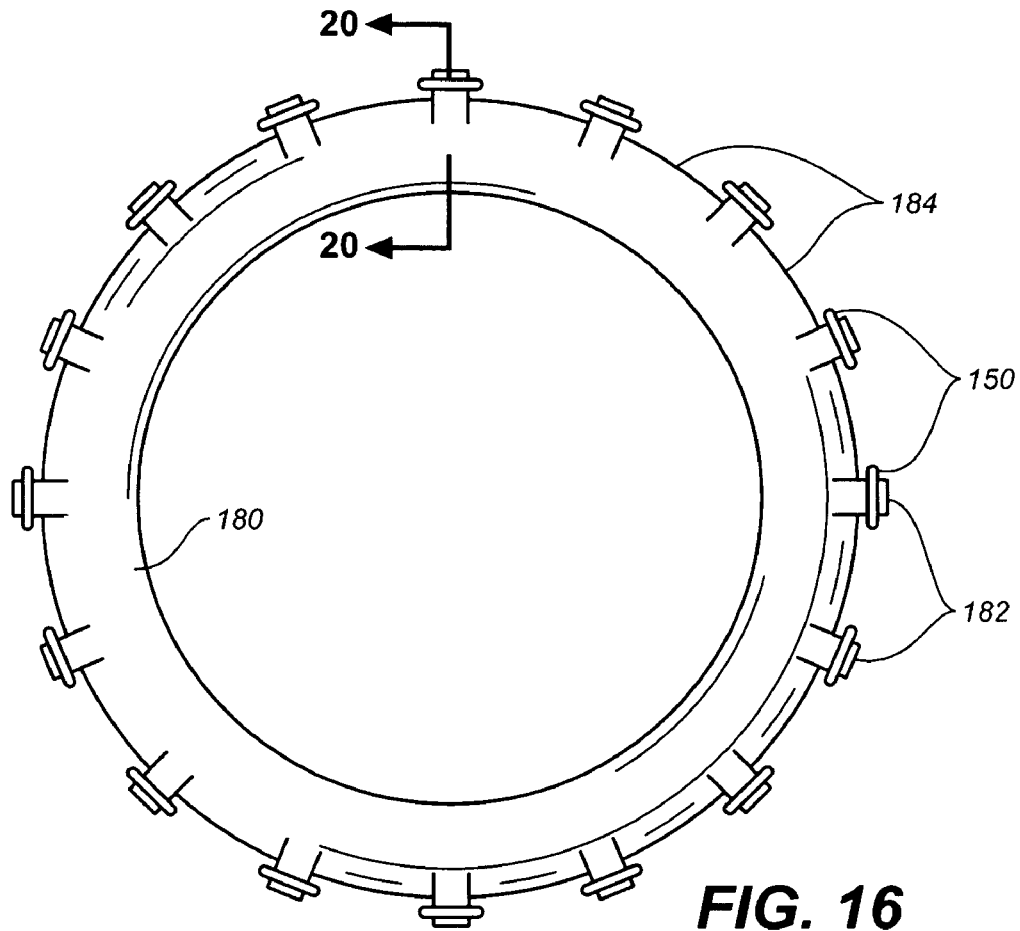
FIG. 16 is a front view a ring member utilized for forming the rolled-up sealing sleeve.
Figure 16A:
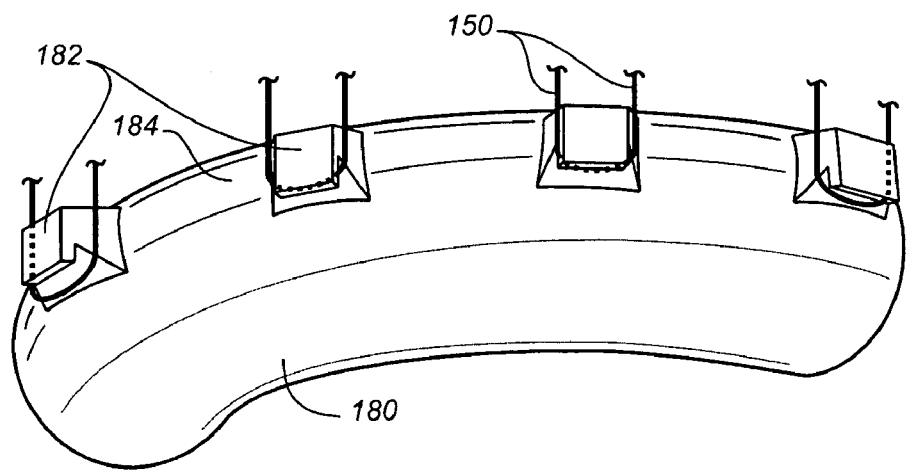
FIG. 16A is a schematic pictorial illustration of a portion of the ring member of FIG. 16.
Figure 17A:
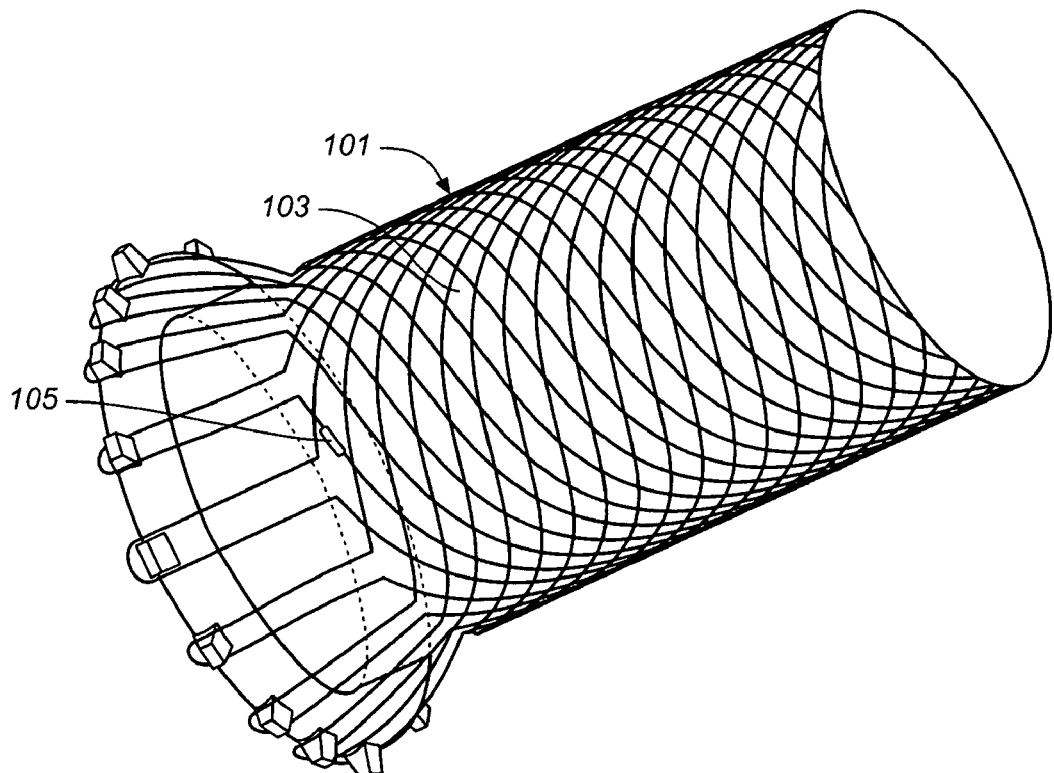
FIGS. 17A-17D are schematic illustrations of the skeletal frame of FIG. 14 with the ring member of FIG. 16 disposed thereon and showing the steps of the process for forming the sealing sleeve.
Figure 17B:
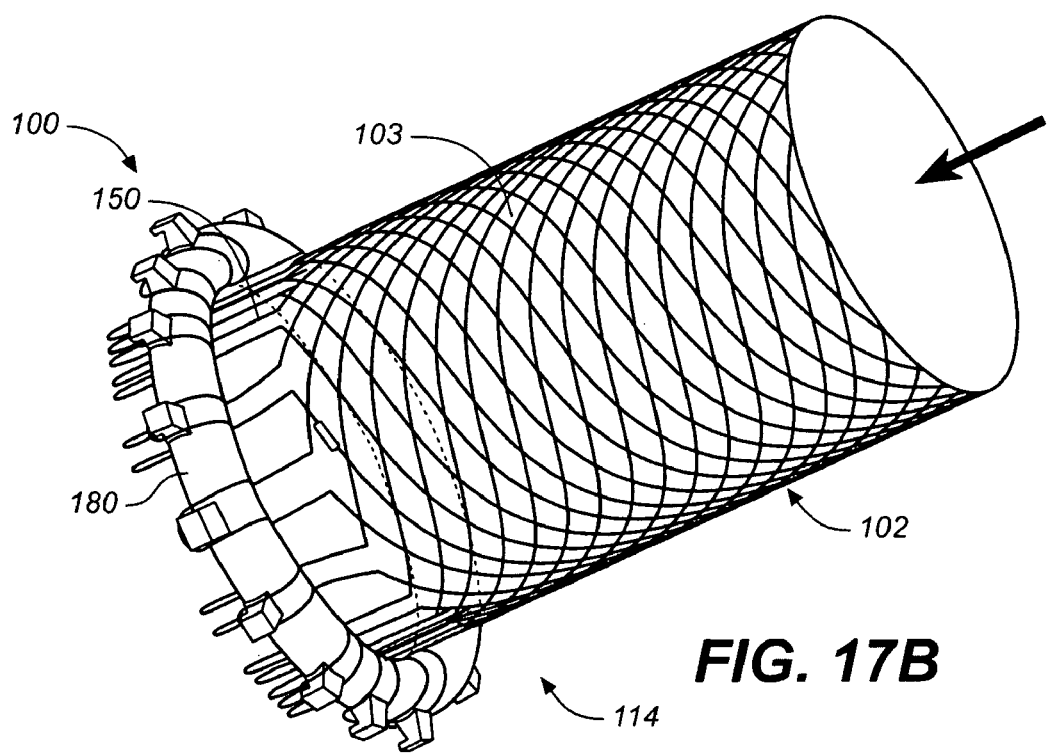
Figure 17C:
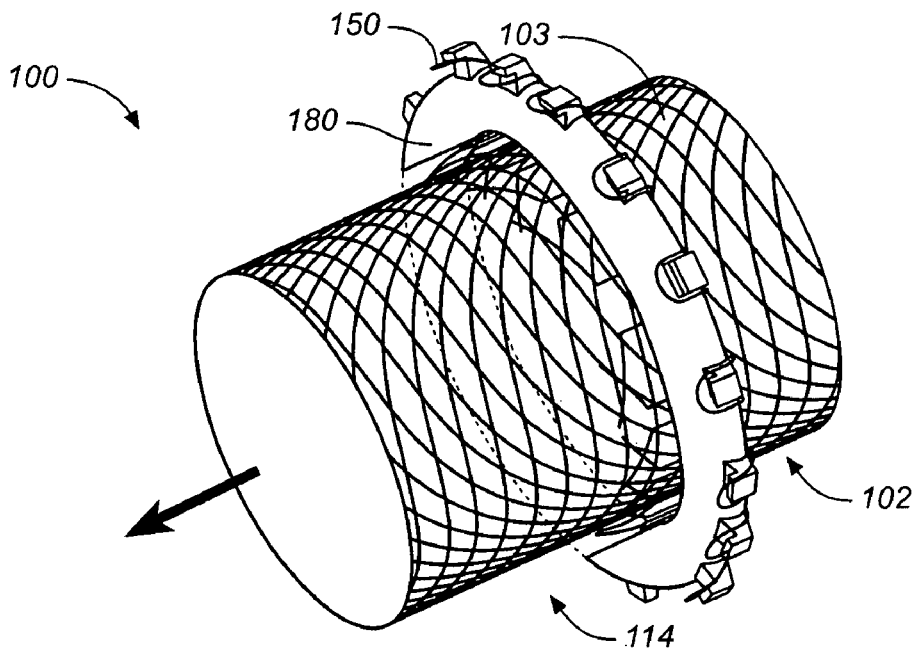
Figure 17D:
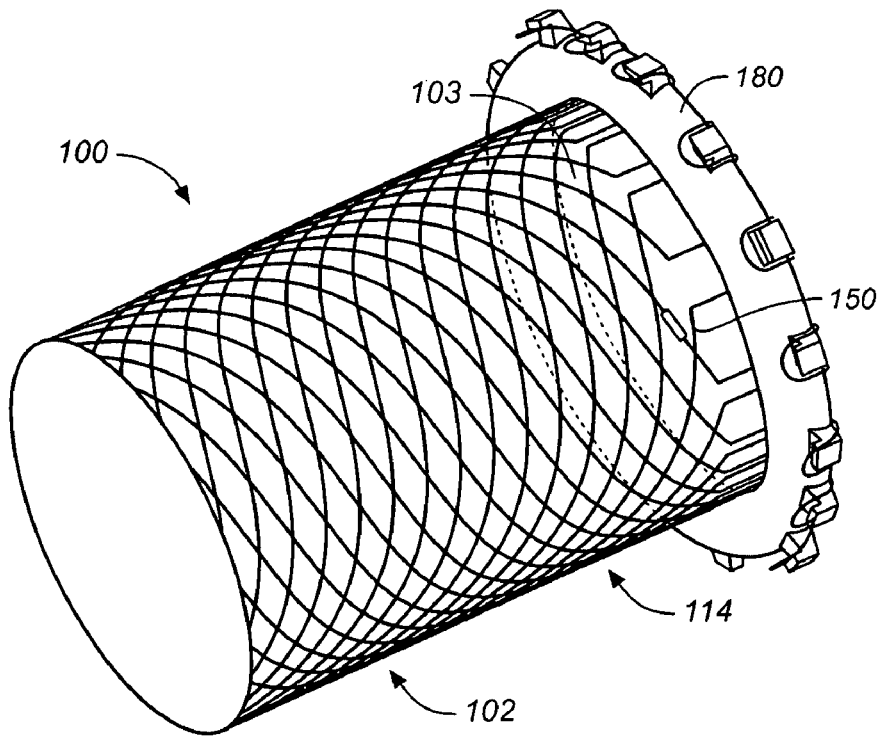
Figure 18:
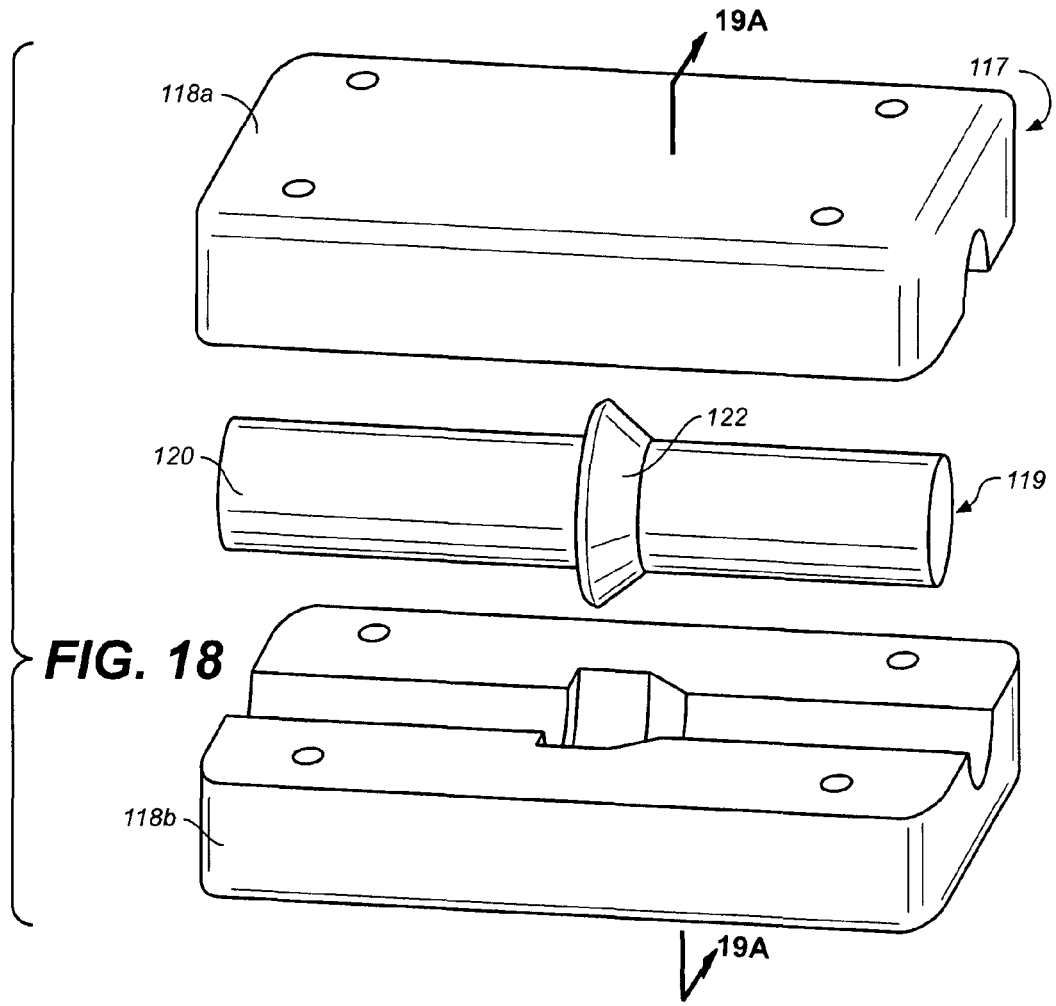
FIG. 18 is a perspective view of a fixture or tool used for forming a branch prosthesis having a tubular body and an annular flange according to an embodiment hereof.
Figure 19:
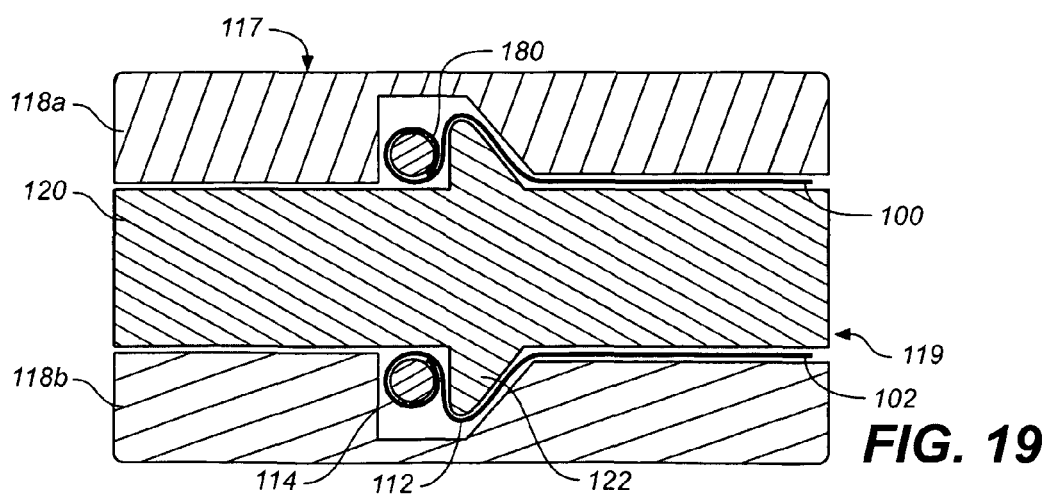
FIG. 19 is a side schematic illustration of the skeletal frame of FIG. 14 inserted within the fixture or tool of FIG. 18.
Figure 20A:
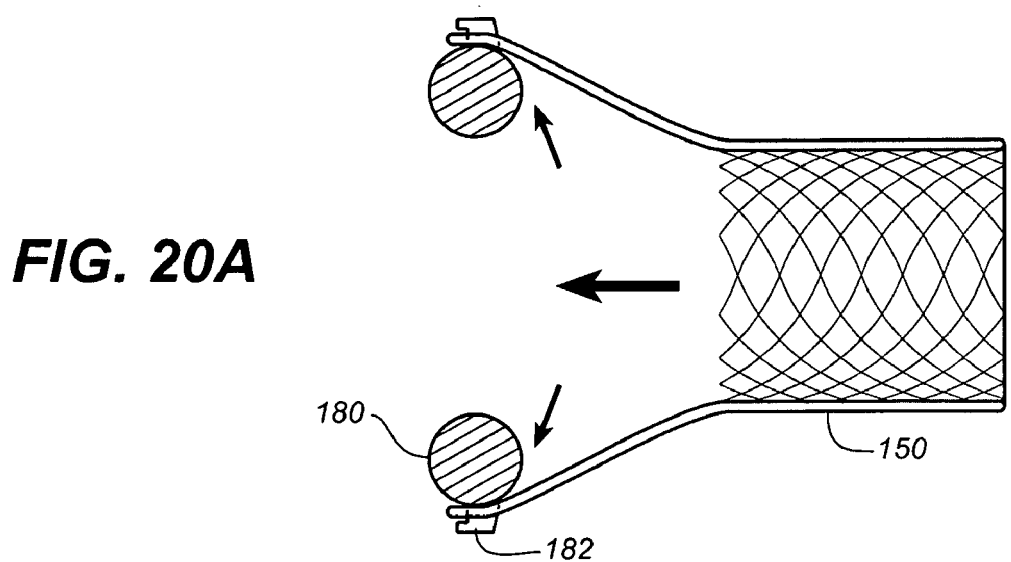
FIGS. 20A-20C and 21A-21C are schematic diagrams illustrating steps of a process for forming the sealing sleeve.
Figure 20B:
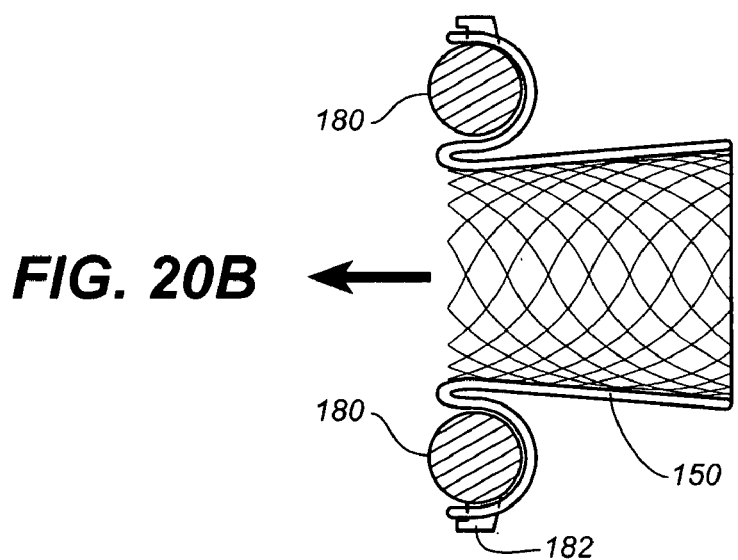
Figure 20C:
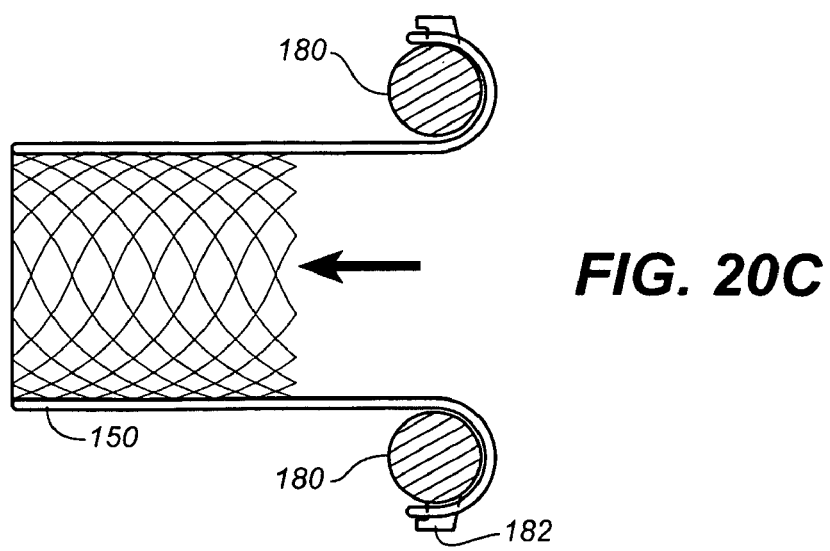
Figure 21A:
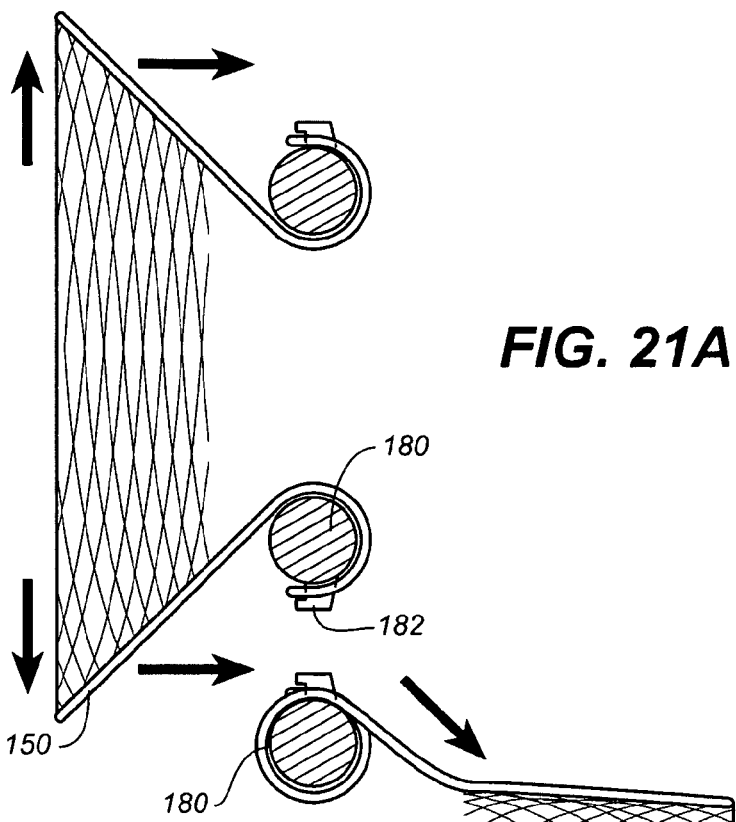
Figure 21B:
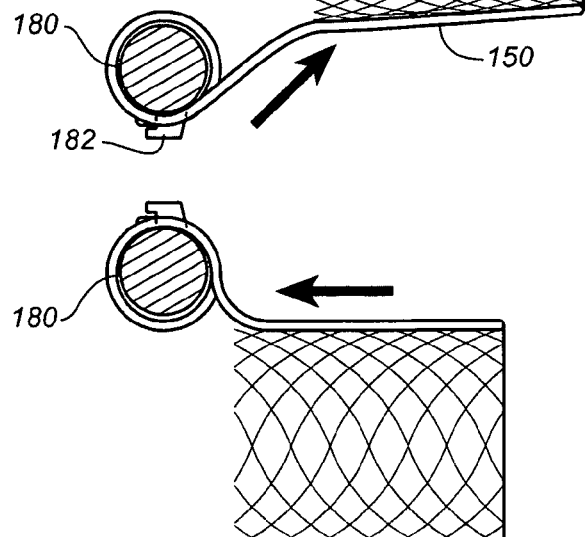
Figure 21C:
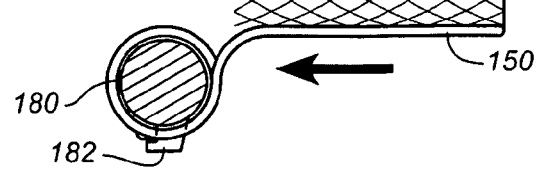

Referring to FIGS. 16-21, in order to form branch prosthesis 100 from skeletal frame 101, skeletal frame 101 undergoes additional processing steps and multiple shape setting cycles to shape sealing assembly 110 thereon. Even though nitinol has an elongation that is several times that of most metals, care must be taken not to stress the nitinol beyond its elastic range. Each of the following processing steps described includes a pause between the next step to perform shape setting (e.g., dipping in a salt pot having a temperature of approximately 500 degrees Celsius—as is well known in the art). More particularly, as shown in FIG. 16, a ring member 180 is provided and may include posts 182 with troughs 184 between the posts 182. Posts 182 may be shaped (for example as hooks) to assist in retaining filaments 150, as shown in FIG. 16A. Other similar means may be used to retain filaments 150 to ring member 180. Ring member 180 inserted over a free or unattached end of filaments 150 and filaments 150 are looped around posts 182, as shown in FIGS. 17A and 20A. Tubular body 102 may then be pushed through the center of ring member 180, as shown in FIGS. 17B-17D and 20B-20C. This results in the tubular body 102 being on the opposite side of ring member 180 and filaments 150 bending around ring member 180. Tubular member 102 may then be expanded and passed over ring member 180, as shown in FIGS. 21A-21B. This results in tubular body 102 returning to its original position relative to ring member 180, and filaments 150 again being around ring member 180. Tubular body 102 may then be passed through the center of ring member 180, as indicated by the arrow in FIG. 21C, to further bend filaments 150 around ring member 180. The number of times that filaments 150 are bent around ring member 180 depends on the elastic limit of the material used for the filaments and the number of rolls desired for the sealing sleeve. Exceeding the elastic limits of the material during roll formation will result in undesirable permanent plastic deformation of the rolled up material.

Further, although the process for forming sealing sleeve 114 has been described with posts 182 disposed on the outer circumference of ring member 180, posts (e.g., 182) could alternatively be disposed on the inner circumference of the ring member, or other locations around ring member 180. If disposed on the inside circumference, tubular member 102 could start to the left of ring member 180, and filaments 150 could be wrapped around the outer circumference of ring member 180 and hooked onto the posts. This would results in a 180° bend in the filaments. Tubular member 102 may then be passed through the middle of the ring member such that the tubular member 102 is on the opposite side of the ring member, and the filaments 150 bend another 180°. Those skilled in the art would recognize possible variations in the method to form the sealing sleeve.

To form the roll up elements and its opposing shoulder, at each heat treating step the skeletal frame 101 is placed within a tool or fixture 117 to undergo heat treatment. Referring to the perspective view of fixture 117 shown in FIG. 18, fixture 117 includes three main components: a first housing 118a, a second housing 118b, and a shaping mandrel 119. Shaping mandrel 119 includes a tubular core 120 and a flared surface 122 that form a triangular or pyramidal bump out. Referring to the side schematic illustration of FIG. 19, skeletal frame 101 having filaments 150 rolled around ring member 180 is placed over shaping mandrel 119 and enclosed within housings 118a, 118b. While encased within fixture 117, skeletal frame 101 is heat set and annealed. Due to the heat treatment, skeletal frame 101 assumes the shape of shaping mandrel 119. More particularly, flared surface 122 of shaping mandrel 119 forms annular flange 112 such that when prosthesis 100 deploys, flange 112 has a triangular cross-section in which the legs of the triangle (formed by flared surface 122) extend radially outward from the outer surface of branch prosthesis 100. In addition, due to the heat treatment, ring member 180 forms sealing sleeve 114 such that when prosthesis 100 deploys, filaments 150 will roll up to a tightly-wound coil when deployed from the constraint of a delivery device. When heat treatment is complete, the filaments 150 are manually unwrapped from the ring member 180 and the ring member is removed and re-used for further processing of other branch prostheses such as these.

In another embodiment hereof, branch prosthesis 100 may be formed from separate or independent components that are attached or otherwise connected together. More particularly, tubular body portion 102 may be an independent component that is subsequently attached to sealing assembly 110. As such, tubular body portion 102 may be any appropriate configuration known to one of skill in the art. For example, in a typical method of making a stent body, a thin-walled, small diameter metallic tube is cut to produce the desired stent pattern, using methods such as laser cutting or chemical etching. The cut stent body may then be de-scaled, polished, cleaned and rinsed. Some examples of methods of forming tubular stent bodies are shown in U.S. Pat. No. 4,733,665 to Palmaz, U.S. Pat. No. 4,800,882 to Gianturco, U.S. Pat. No. 4,886,062 to Wiktor, U.S. Pat. No. 5,133,132 to Wiktor, U.S. Pat. No. 5,292,331 to Boneau, U.S. Pat. No. 5,421,955 to Lau, U.S. Pat. No. 5,935,162 to Dang, U.S. Pat. No. 6,090,127 to Globerman, and U.S. Pat. No. 6,130,116 to Wolinsky et al., each of which is incorporated by reference herein in its entirety.

When formed separately, tubular body portion 102 and sealing assembly 110 may be connected or joined in any suitable manner known in the art. For example, tubular body portion 102 and sealing assembly 110 may be welded together such as by resistance welding, friction welding, laser welding or another form of welding such that no additional materials are used to connect tubular body portion 102 and sealing assembly 110. Alternatively, tubular body portion 102 and sealing assembly 110 can be connected by soldering, by the addition of a connecting element there between, or by another mechanical method. Other connections or ways to connect tubular body portion 102 and sealing assembly 110 would be apparent to one skilled in the art and are included herein.

Branch prosthesis 100 may be delivered by any suitable delivery system. For example, FIG. 8 illustrates a schematic side view of an exemplary delivery system for delivering and deploying self-expanding branch prosthesis 100. The delivery system includes a retractable outer shaft 130 having a proximal end 132 and a distal end 136, and an inner shaft 138 having a proximal end 140 and a distal end 142. Outer shaft 130 defines a lumen extending there through (not shown), and inner shaft 138 slidably extends through the lumen of outer shaft 130 to a distal tip 144 of the delivery system. Distal tip 144 is coupled to distal end 142 of inner shaft 138, and may be tapered and flexible to provide trackability in tight and tortuous vessels. In an embodiment, inner shaft 138 may define a guidewire lumen (not shown) for receiving a guidewire (not shown) there through. When the guidewire lumen is present, inner shaft 138 may be advanced over an indwelling guidewire to track the delivery system to the target site. Alternatively, inner shaft 138 may instead be a solid rod (not shown) without a lumen extending there through. In an embodiment where inner shaft 138 is a solid rod, inner shaft 138 is tracked to the target site with the assistance of tapered distal tip 144.

Branch prosthesis 100 may be mounted on distal end 142 of inner shaft 138 such that sealing assembly 110 is more proximal with respect to the hub of the delivery system than tubular body 102. Outer shaft 130 is provided to cover branch prosthesis 100 (not shown in FIG. 8) mounted on the distal end 142 of inner shaft 138 while the delivery system is tracked through a body lumen to the deployment site. Outer shaft 130 is movable in an axial direction along and relative to inner shaft 138 and extends to a proximal portion of the delivery system where it may be controlled via an actuator, such as a handle 134, to selectively expand branch prosthesis 100 mounted on distal end 142 of inner shaft 138. Outer shaft 130 in a non-retracted position contains branch prosthesis 100 in a constrained diameter configuration. In the constrained configuration, filaments 150 are unwound from ring member 180 and are straightened. Outer shaft 130 constrains filaments 150 in the straightened configuration until deployment thereof. Handle 134 may be a push-pull actuator that is coupled to proximal end 132 of outer shaft 130. To expand branch prosthesis 100, while holding proximal end 140 of inner shaft 138 fixed, handle 134 is pulled in order to retract outer shaft 130 in the direction of arrow 146. Alternatively, the actuator may be a rotatable knob (not shown) that is coupled to proximal end 132 of outer shaft 130 such that when the knob is rotated, outer shaft 130 is retracted in the direction of arrow 146 to expand branch prosthesis 100. Thus, when the actuator is operated, i.e., manually turned or pulled, outer shaft 130 is retracted over inner shaft 138 in a proximal direction as indicated by directional arrow 146. As illustrated in FIG. 8, outer shaft 130 is in a non-retracted, delivery configuration. Although described as a full-length retractable sheath, it should be understood that outer shaft 130 may alternatively be a relatively short graft cover, i.e., only slightly longer than the length of branch prosthesis 100. The relatively short graft cover is proximally retractable with respect to the hub of the delivery system by being coupled to an actuator at the proximal end of the delivery device, such as a push-pull handle device or rotatable knob as described above, via one or more connecting elements extending between the graft cover and the actuator.

When outer shaft 130 is retracted proximally with respect to the hub of the delivery system, self-expanding branch prosthesis 100 is released and allowed to assume its expanded configuration. When using the delivery system of FIG. 8 with branch prosthesis 100 mounted such that sealing assembly 110 is more proximal with respect to the hub of the delivery system than tubular body 102, tubular body 102 will be deployed or unsheathed first as outer shaft 130 is retracted in the direction of arrow 146. More specifically, tubular body 102 is initially deployed, followed by deployment of annular flange 112 and lastly, sealing sleeve 114 is released and allowed to assume its rolled-up or coiled configuration. In this manner, annular flange 112 first presses against the perimeter of the fenestration along an outer surface of a deployed main prosthesis. Sealing sleeve 114 is then deployed, rolling up against the perimeter of the fenestration along an inner surface of the deployed main prosthesis, in apposition to deployed flange 112. In one embodiment, the sealing sleeve rolls up to a coil such that a proximal end of the sealing sleeve turns at least 270 degrees towards the flange. In some embodiments, the sealing sleeve rolls up to a coil such that a proximal end of the sealing sleeve turns towards the flange, such that the proximal end of the sealing sleeve contacts a portion of the sealing sleeve distal of the proximal end. The delivery system of FIG. 8 may be useful when delivering branch prosthesis 100 into a target branch vessel through a deployed main vessel prosthesis, as described herein with respect to FIGS. 11-13. For example, the deployed main vessel prosthesis may be located within the aortic arch, descending aorta, or abdominal aorta and branch prosthesis 100 may be introduced into the vasculature through a branch of the femoral artery.

Branch prosthesis 100 may be mounted on distal end 142 of inner shaft 138 by any suitable configuration known in the art. For example, attachment bands extending between branch prosthesis 100 and the inner shaft may be used for acting as a means for retaining branch prosthesis 100 in place during delivery. The attachment bands eventually release branch prosthesis 100 by self-expansion of the attachment bands. Other means may be used for retaining branch prosthesis 100 in place within delivery system during delivery. For example, branch prosthesis 100 may be held in frictional engagement with the delivery system by the inclusion of slots, ridges, pockets, or other prosthesis retaining features (not shown) formed into the exterior surface of the inner shaft to further ensure secure mounting of branch prosthesis 100 as it is tracked transluminally to the target site. In addition, a cap may be coupled to the distal end of the inner shaft to retain branch prosthesis 100 in a radially compressed configuration. An actuator at the proximal portion of the delivery system may precisely control the release of branch prosthesis 100 from the cap and from the radially compressed configuration. Such delivery systems may be the delivery system described in U.S. Pat. No. 7,264,632 to Wright et al., which is hereby incorporated by reference in its entirety, or other such similar delivery systems that are well known in the art.

Inner and outer shafts 130, 138 may be constructed of any suitable flexible polymeric material. Non-exhaustive examples of material for the catheter shafts are polyethylene terephalate (PET), nylon, polyethylene, PEBAX, or combinations thereof, either blended or co-extruded. Optionally, a portion of the catheter shafts may be constructed as a composite having a reinforcement material incorporated within a polymeric body to enhance strength, flexibility, and/or toughness. Suitable reinforcement layers include braiding, wire mesh layers, embedded axial wires, embedded helical or circumferential wires, and the like. In an embodiment, the proximal portions of the catheter shafts may in some instances be constructed from a reinforced polymeric tube, for example, as shown and described in U.S. Pat. No. 5,827,242 to Follmer et al. which is incorporated by reference herein in its entirety. The catheter shafts may have any suitable working length, for example, 550 mm-600 mm, to extend to a target location where branch prosthesis 100 is to be implanted.

FIG. 9 illustrates a schematic side view of an alternate delivery system for delivering and deploying self-expanding branch prosthesis 100. The delivery system includes a relatively short graft cover 930 having a proximal end 932 and a distal end 936, and an inner shaft 938 having a proximal end 940 and a distal end 942. Similar to the embodiment depicted above, inner shaft 938 may or may not define a guidewire lumen (not shown) and may include a tapered and flexible distal tip 944 coupled to distal end 942 to provide trackability in tight and tortuous vessels. Branch prosthesis 100 may be mounted on distal end 942 of inner shaft 938 such that sealing assembly 110 is more distal than tubular body 102 with respect to the hub of the delivery system. Branch prosthesis 100 may be mounted by any suitable configuration known in the art, such as those described above with respect to FIG. 8.

Graft cover 930 is provided to cover and constrain branch prosthesis 100 (not shown in FIG. 9) mounted on the distal end 942 of inner shaft 938 while the delivery system is tracked through a body lumen to the deployment site. Graft cover 930 is relatively short, i.e., only slightly longer than the length of branch prosthesis 100. Graft cover 930 is attached to a pusher rod 941, which extends inside a lumen (not shown) of inner shaft 938 such that a proximal end thereof exits out of proximal end 940 of inner shaft 938. Pusher rod 941 is movable in an axial direction within and relative to inner shaft 938 and may be manipulated by an operator to selectively expand branch prosthesis 100. To expand branch prosthesis 100, while holding proximal end 940 of inner shaft 938 fixed, pusher rod 941 (and attached graft cover 930) are distally advanced as indicated by directional arrow 947 in order to uncover or unsheathe branch prosthesis 100. Once branch prosthesis 100 is completely uncovered and expanded, the delivery system is retracted into the expanded lumen of branch prosthesis 100 and removed from the patient. Although not shown in FIG. 9, it should be understood that the proximal end of pusher rod 941 may be coupled to an actuator for expanding branch prosthesis 100, such as a push-pull handle device or rotatable knob as described above with respect to FIG. 8.

When graft cover 930 is distally advanced with respect to the hub of the delivery system, self-expanding branch prosthesis 100 is released and allowed to assume its expanded configuration. Utilizing the delivery system of FIG. 9 with branch prosthesis 100 mounted such that sealing assembly 110 is more distal with respect to the hub of the delivery system than tubular body 102, tubular body 102 will be deployed or unsheathed first as graft cover 930 is distally advanced via pusher rod 941 in the direction of arrow 947. More specifically, tubular body 102 is initially deployed, followed by deployment of annular flange 112 and lastly, sealing sleeve 114 is released and allowed to assume its rolled-up or coiled configuration in apposition to deployed flange 112. The delivery system of FIG. 9 may be useful when delivering branch prosthesis 100 to a target branch vessel through the target side branch vessel. For example, branch prosthesis 100 may be introduced into the vasculature through a carotid artery via an auxiliary artery in order to be delivered through the target branch vessel.

Figure 10:
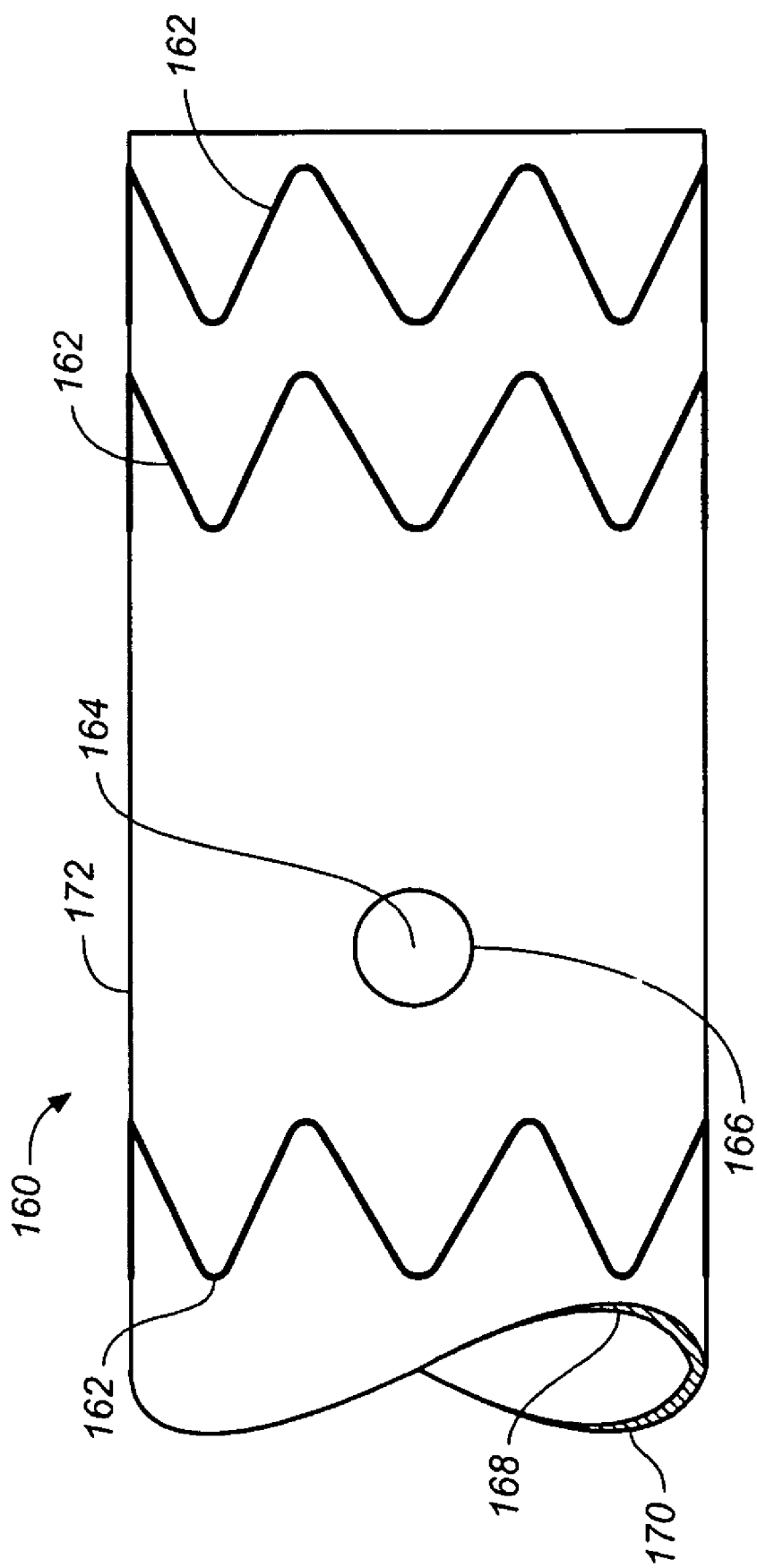
FIG. 10 is an example of a main vessel prosthesis for utilization with the branch prosthesis of FIG. 1.

As previously mentioned, branch prosthesis 100 is configured for use in conjunction with a main vessel prosthesis having a side opening and deployed within in a main vessel. An exemplary main prosthesis is depicted in FIG. 10. Main prosthesis 160 includes a synthetic graft material shaped as a tubular body 172. Main prosthesis 160 includes annular support members or stents 162 attached thereto for supporting the ends thereof. FIG. 10 illustrates three stents 162 attached to the graft material; however, a greater or lesser number of stents may be utilized. Stents 162 may have any suitable configuration. Examples of such annular support structures are described, for example, in U.S. Pat. Nos. 5,713,917 and 5,824,041, which are incorporated by reference herein in their entirety. When used in an aneurysm exclusion device, the stents have sufficient radial spring force and flexibility to conformingly engage the prosthesis with the body lumen inner wall, to avoid excessive leakage, and prevent pressurization of the aneurysm, i.e., to provide a leak-resistant seal. Although some leakage of blood or other body fluid may occur into the aneurysm isolated by the graft prosthesis, an optimal seal will reduce the chances of aneurysm pressurization and resulting rupture. Stent 162 is preferably a self-expanding spring member that is deployed by release from a restraining mechanism, such as a sheath. For example, stent 162 may be constructed of a superelastic material, such as nitinol. In the depicted embodiment, an intermediate portion of main prosthesis 160 is solely graft material having no radial support along its length, i.e., is stent-free and unsupported. The unsupported body portion is flexible permitting placement of the prosthesis in a highly curved anatomy such as the aortic arch. However, the presence and length of the unsupported body portion may vary depending on the desired application.

Main prosthesis 160 includes a fenestration or opening 164 having a perimeter 166 in a sidewall of main prosthesis 160. Fenestration 164 extends from an inner surface 168 of main prosthesis 160 to an outer surface 170 of main prosthesis 160, and is used to permit blood flow into a side branch vessel. As depicted in FIG. 10, fenestration 164 may be pre-formed on main prosthesis 160 prior to insertion of the main prosthesis into the patient. Alternatively, fenestration 164 may be formed in situ after main prosthesis 160 has been deployed in the target vessel, as will be explained in more detail below with respect to FIG. 10.

Figure 11:
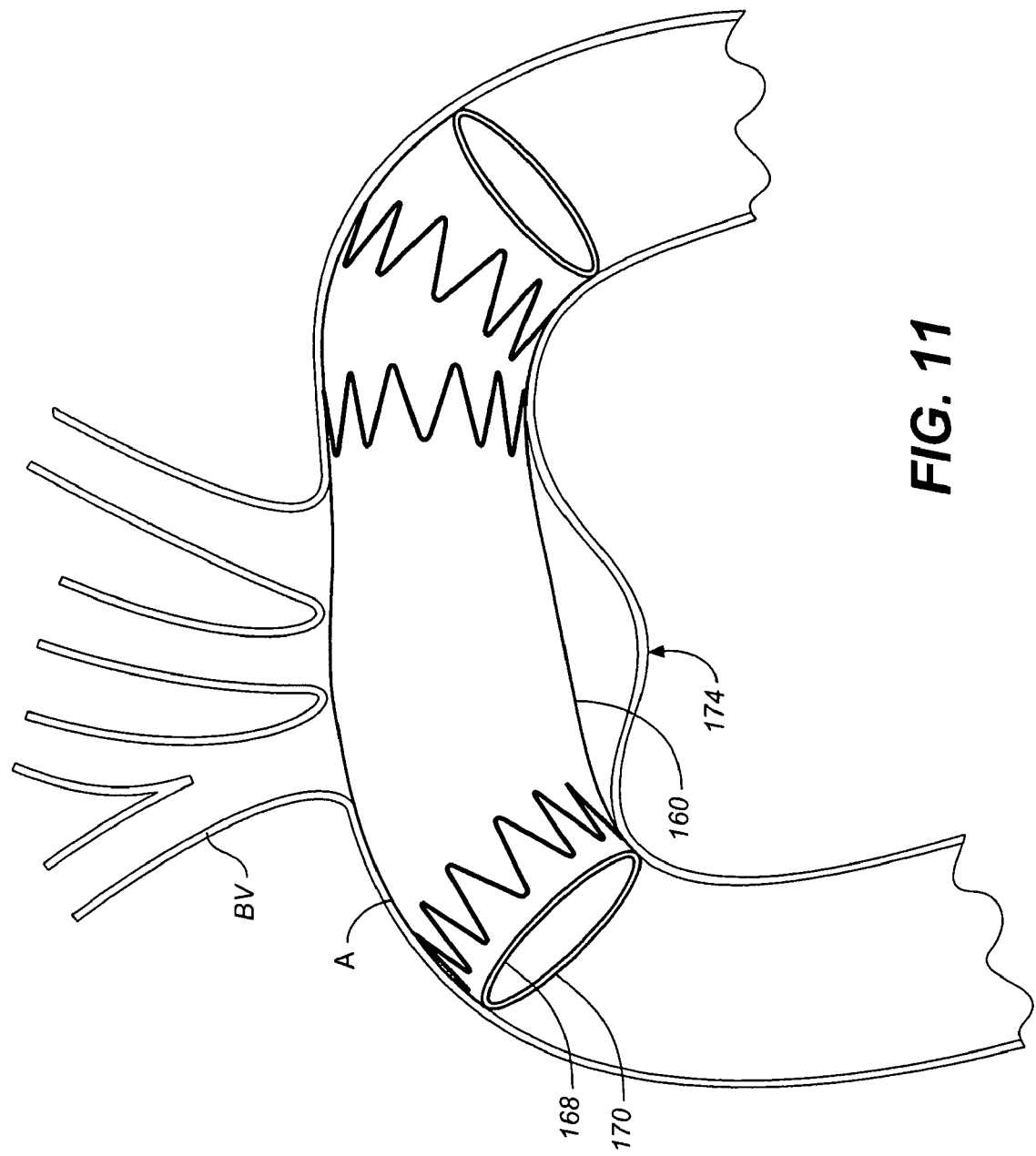
FIGS. 11-13 illustrate a method for forming a fluid-tight seal between a main prosthesis and a branch prosthesis according to an embodiment hereof.
Figure 12:
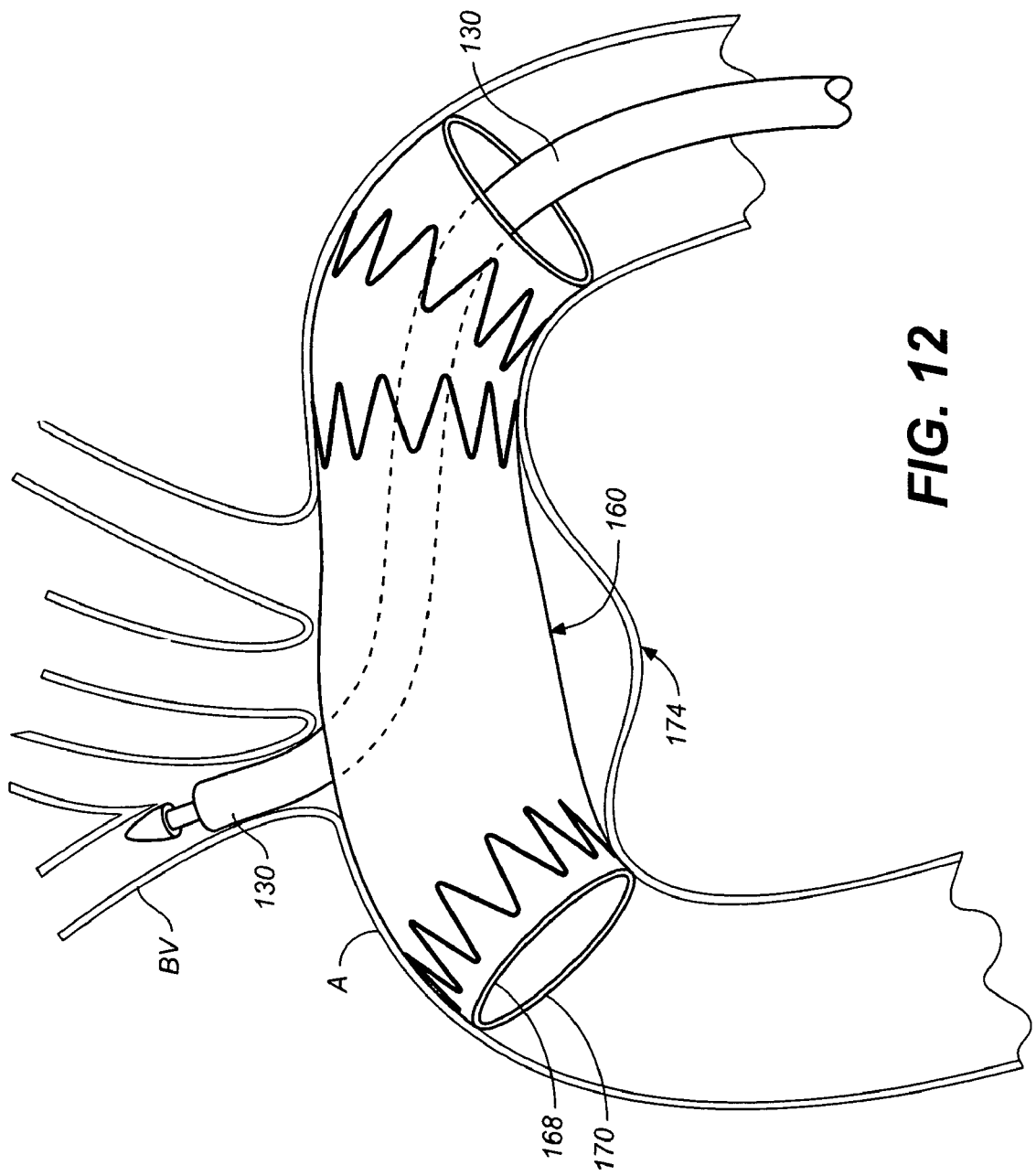
Figure 13:
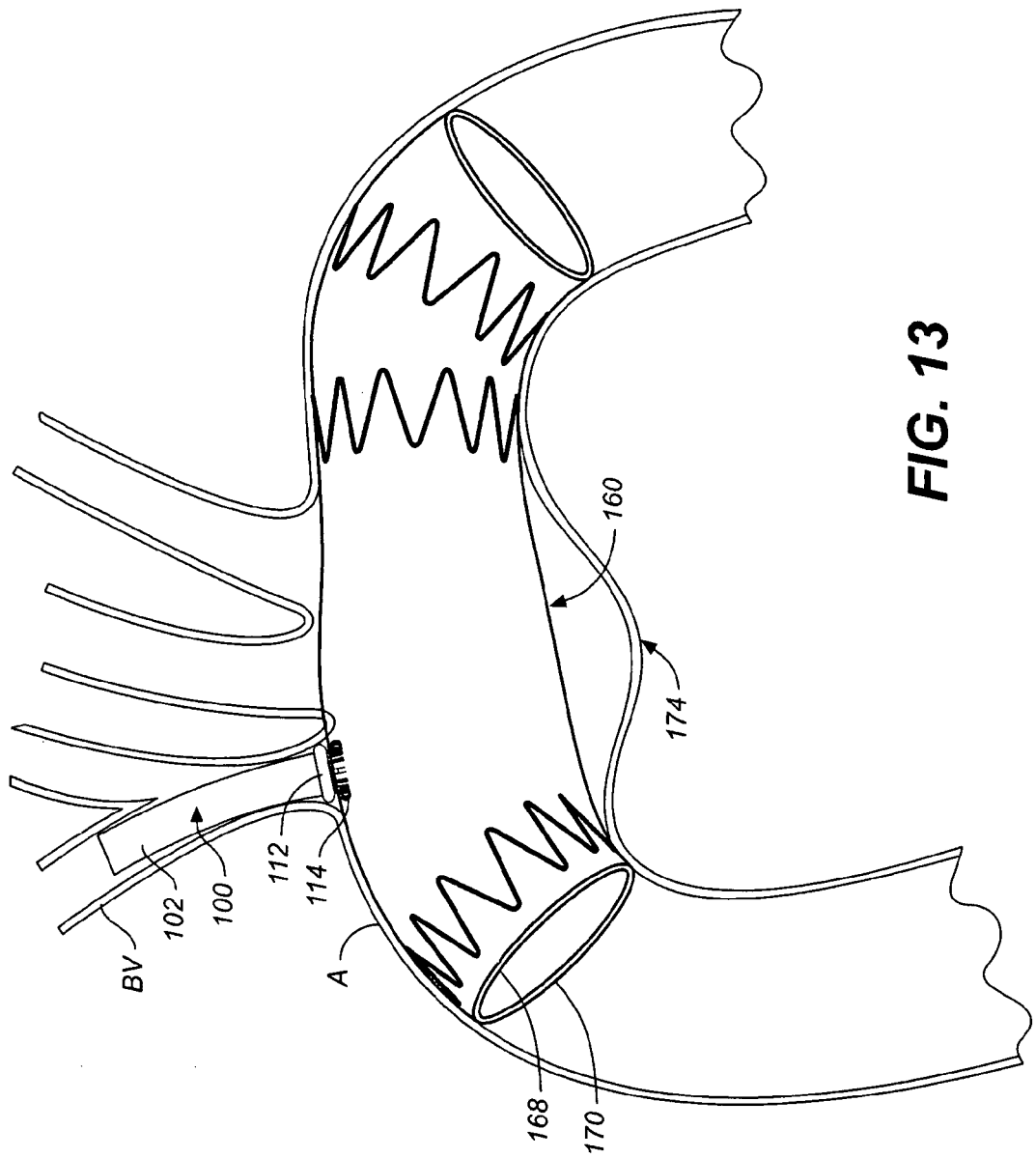

Referring now to FIGS. 11-13, a method for forming a fluid-tight seal between a main prosthesis and a branch prosthesis according to an embodiment hereof is described. FIG. 11 is a side view of main prosthesis 160 deployed within the aorta (labeled A in FIGS. 11-13), more specifically, deployed within the aortic arch. The aortic arch has multiple side branch vessels extending therefrom, including the left subclavian artery, the left common carotid artery, and the brachiocephalic artery which further branches into the right subclavian artery and the right common carotid artery. The following method of forming a fluid-tight seal between a main prosthesis and a branch prosthesis is described to provide perfusion to the brachiocephalic artery (labeled BV in FIGS. 11-13), but it will be understood that the method may be utilized for providing perfusion to the left subclavian artery or the left common carotid artery, as well as side branch vessels of other vessels other than the aortic arch. For example, the method may be utilized for providing perfusion to side branch vessels off the abdominal aorta, such as the renal arteries.

Still referring to FIG. 11, deployed main prosthesis 160 spans aneurysm 174. If main prosthesis 160 is a pre-fenestrated graft, main prosthesis 160 is positioned within aorta A such that fenestration 164 (not visible in FIG. 11) aligns with the ostium of branch vessel BV. Alternatively, fenestration 164 may be created in situ to perfuse branch vessel BV. A separate puncture device may be delivered to create fenestration 164, such as a dilator-needle combination device having a pointed tip sufficient for puncturing through the graft material of main prosthesis 160. Embodiments of the present structure may be used with any conventional puncture device capable of creating a fenestration in main prosthesis 160. For example, the puncture device may be any puncture device known in the art, e.g., biopsy needle, RF dome electrode, or RF ring electrodes, including but not limited to those shown or described in US patent application of Bruszewski et al. U.S. Ser. No. 11/939,106, filed 6 Mar. 2008, incorporated in its entirety by reference herein.

Referring now to FIG. 12, a delivery system carrying branch prosthesis 100 is shown as delivered to target branch vessel BV. For example, a delivery system as described above with respect to FIG. 8 may be utilized for delivering branch prosthesis 100. The delivery system, and thus branch prosthesis 100, may be introduced into the vasculature through a branch of the femoral artery and delivered to branch vessel BV through the deployed main prosthesis 160. The delivery system extends through the deployed main prosthesis 160, and into the branch vessel BV via fenestration 164 (not visible in FIG. 12). Retractable shaft 130 restrains branch prosthesis 100 in a compressed configuration and prevents it from damaging or catching on the luminal wall as it is delivered to the aneurysm site. Surgical methods and apparatus for delivering the graft intravascularly are generally known in the art and may be used to place the graft delivery system within the vasculature and deliver the graft to the deployment site. For example, the graft may be guided to the deployment site using fluoroscopic imaging. It should be understood by those of ordinary skill in the art that branch prosthesis 100 may alternatively be delivered into the vasculature through a carotid artery via an auxiliary artery and delivered through branch vessel BV by a delivery system such as described above with respect to FIG. 9.

Once branch vessel prosthesis 100 is positioned as desired within branch vessel BV, outer shaft 130 is retracted in a proximal direction with respect to the hub of the delivery system to allow branch prosthesis 100 to self-expand into apposition with the vessel wall. As outer shaft 130 is retracted, tubular body 102 is initially deployed within branch vessel BV, followed by deployment of annular flange 112 and lastly, sealing sleeve 114 is released and allowed to assume its rolled-up or coiled configuration. In this manner, annular flange 112 first presses against perimeter 166 of fenestration 164 along outer surface 170 of deployed main prosthesis 160. Sealing sleeve 114 is then deployed, rolling up against perimeter 166 of fenestration 164 along inner surface 168 of deployed main prosthesis 160, in apposition to deployed flange 112. Sealing sleeve 114 captures the cloth or material of main prosthesis 160 and presses it against annular flange 112 to form a fluid-tight seal between main prosthesis 160 and branch prosthesis 100 (see also FIG. 4). Branch prosthesis 100 serves as a conduit to direct blood flow through fenestration 164 of main prosthesis 160 into the lumen of branch vessel BV. As shown in FIG. 13, branch prosthesis 100 is in its deployed or expanded configuration and the delivery system is removed from the patient.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A main prosthesis and a branch prosthesis assembly comprising:
   a main prosthesis configured for placement in a main vessel, the main prosthesis including an outer surface, an inner surface, and a side opening having a perimeter; and
   a branch prosthesis configured for placement in a branch vessel that extends from the main vessel, the branch prosthesis having a radially compressed first configuration and a radially expanded second configuration, the branch prosthesis including:
   an expandable tubular body portion with a first outer diameter in the second configuration, the body portion having a proximal end and a distal end;
   an expandable annular flange coupled to the proximal end of the body portion, the flange having a second outer diameter in the second configuration that is greater than the first outer diameter; and
   a sealing sleeve extending proximally from the expandable flange, wherein the sealing sleeve is a generally straight cylindrical hollow shape in the first configuration and the sealing sleeve is a rolled-up coil with a proximal end having at least a 270 degree turn towards the flange in the second configuration,
   wherein in the second configuration, the annular flange engages the outer surface of the main prosthesis around the perimeter of the side opening and the sealing sleeve engages the inner surface of the main prosthesis around the perimeter of the side opening to form a seal between the main prosthesis and the branch prosthesis.

2. The prosthesis of claim 1, wherein the body portion is an expandable single wire nitinol (NiTi) braid.

3. The prosthesis of claim 2, wherein the body portion is impermeable by elastomer impregnation, lamination of elastomer film, or lamination of ePTFE film.

4. The prosthesis of claim 1, wherein the body portion and flange are an integral expandable single wire nitinol braid.

5. The prosthesis of claim 4, wherein the single wire extends from the flange to the sealing sleeve and includes straight members having loops at proximal ends thereof.

6. The prosthesis of claim 1, wherein the flange and sealing sleeve are formed as one-piece and subsequently attached to the body portion.

7. The prosthesis of claim 1, wherein the body portion, flange, and sealing sleeve are formed from an expandable single wire nitinol (NiTi) braid, the braid being impermeable by elastomer impregnation, lamination of elastomer film, or lamination of ePTFE film.

8. The prosthesis of claim 1, wherein the flange and sealing sleeve are formed from nitinol (NiTi).

9. The prosthesis of claim 1, wherein the body portion has a length between 40 mm and 60 mm.

10. The prosthesis of claim 1, wherein the sealing sleeve has a length between 1 cm and 3 cm when in the first configuration.

11. The prosthesis of claim 1, wherein the first outer diameter of the body portion is between 5 mm and 8 mm.

12. The prosthesis of claim 1, wherein the first outer diameter of the body portion is between 8 mm and 14 mm.

13. The prosthesis of claim 1, wherein the flange has a triangular cross-section.

14. The prosthesis of claim 1, wherein the body portion includes a graft material.

15. The prosthesis of claim 14, wherein the graft material is selected from the group consisting of woven polyester, expanded polytetrafluoroethylene, Dacron, polyurethane, and silicone.

16. A method for forming a seal between a main prosthesis and a branch prosthesis, comprising the steps of:
deploying the main prosthesis in a main vessel, wherein a side opening of the main prosthesis is substantially aligned with a branch vessel;
delivering the branch prosthesis in a radially compressed first configuration to the branch vessel, wherein the branch prosthesis includes:
a tubular body portion having a proximal end and a distal end;
an annular flange coupled to the proximal end of the body portion; and
a sealing sleeve extending proximally from the expandable flange, wherein the sealing sleeve is a generally straight cylindrical hollow shape in the first configuration,
positioning the annular flange adjacent an outer surface of the main prosthesis and the sealing sleeve adjacent an inner surface of the main prosthesis; and
deploying the branch prosthesis from the first configuration to a radially expanded second configuration wherein the tubular portion expands to a first outer diameter, the annular flange expands to a second outer diameter larger than the first outer diameter and engages the outer surface of the main prosthesis around a perimeter of the side opening, and the sealing sleeve rolls up to a coil such that a proximal end of the sealing sleeve turns at least 270 degrees towards the flange and engages the inner surface of the main prosthesis around the perimeter of the side opening to form a seal between the main prosthesis and the branch prosthesis.

17. The method of claim 16, wherein the side opening of the main prosthesis is formed in situ subsequent to deploying the main prosthesis in the main vessel.

18. The method of claim 17, wherein main vessel is the aortic arch.

19. The method of claim 17, wherein the step of delivering the branch prosthesis in a radially compressed first configuration comprises delivering the branch prosthesis through the main prosthesis and through the side opening of the main prosthesis into the branch vessel.

20. The method of claim 17, wherein the step of delivering the branch prosthesis in a radially compressed first configuration comprises delivering the branch prosthesis through the branch vessel and delivering the proximal end of the branch prosthesis through the side opening of the main prosthesis into the main prosthesis.

21. The method of claim 16, wherein the side opening of the main prosthesis is pre-formed prior to deploying the main prosthesis in the main vessel.

22. A method for deploying a branch prosthesis in a branch vessel, comprising the steps of:
delivering the branch prosthesis in a radially compressed first configuration intraluminally into the branch vessel, wherein the branch prosthesis includes:
a tubular body portion having a proximal end and a distal end;
an annular flange coupled to the proximal end of the body portion; and
a sealing sleeve extending proximally from the expandable flange, wherein the sealing sleeve is a generally straight cylindrical hollow shape in the first configuration,
positioning the annular flange adjacent a junction of a main vessel and the branch vessel; and
deploying the branch prosthesis from the first configuration to a radially expanded second configuration wherein the tubular portion expands to a first outer diameter, the annular flange expands to a second outer diameter larger than the first outer diameter, and the sealing sleeve rolls up to a coil such that a proximal end of the sealing sleeve turns 360 degrees towards the flange such that the proximal end of the sealing sleeve contacts a portion of the sealing sleeve distal of the proximal end.

* * * * *